(12) United States Patent
Herbert

(10) Patent No.: US 8,211,053 B2
(45) Date of Patent: Jul. 3, 2012

(54) INTEROSMOLAR FLUID REMOVAL

(75) Inventor: Curtis B. Herbert, Blaine, MN (US)

(73) Assignee: Equilibrate, LLC, Blaine, MN (US)

( * ) Notice: Subject to any disclaimer, the term of this patent is extended or adjusted under 35 U.S.C. 154(b) by 725 days.

(21) Appl. No.: 12/317,117

(22) Filed: Dec. 19, 2008

(65) Prior Publication Data

US 2009/0287178 A1   Nov. 19, 2009

Related U.S. Application Data

(60) Provisional application No. 61/127,440, filed on May 13, 2008, provisional application No. 61/137,921, filed on Aug. 5, 2008.

(51) Int. Cl.
*A61M 1/00* (2006.01)

(52) U.S. Cl. .......................................... 604/29

(58) Field of Classification Search .................... 604/29, 604/892.1, 28
See application file for complete search history.

(56) References Cited

U.S. PATENT DOCUMENTS

| | | | |
|---|---|---|---|
| 3,115,138 A | 12/1963 | McElvenny et al. | |
| 3,707,967 A | 1/1973 | Kitrilakis et al. | |
| 3,752,158 A * | 8/1973 | Kariher | 604/133 |
| 3,880,164 A * | 4/1975 | Stepno | 604/131 |
| 4,276,175 A | 6/1981 | Bower | |
| 4,299,222 A | 11/1981 | Eckenhoff | |
| 4,437,856 A | 3/1984 | Valli | |
| 4,603,699 A | 8/1986 | Himpens | |
| 4,681,570 A | 7/1987 | Dalton | |
| 4,729,762 A | 3/1988 | Doumenis | |
| 4,892,518 A | 1/1990 | Cupp et al. | |
| 4,898,582 A | 2/1990 | Faste | |
| 4,960,415 A | 10/1990 | Reinmuller | |
| 4,990,137 A | 2/1991 | Graham | |
| 5,024,663 A | 6/1991 | Yum | |

(Continued)

FOREIGN PATENT DOCUMENTS

EP  1 852 136 A1  7/2007

(Continued)

OTHER PUBLICATIONS

Ben-Sasson et al., "Osmosis: A Macroscopic Phenomenon, A Microscopic View", Advances in Physiology Education, 27(1):15-19, Mar. 2003.

(Continued)

*Primary Examiner* — Kevin C Sirmons
*Assistant Examiner* — Bradley Osinksi
(74) *Attorney, Agent, or Firm* — Dardi & Herbert, PLLC; Curtis B. Herbert

(57) ABSTRACT

There are many medical situations that require removal of fluid from a patient. There are many ways to remove the fluid but many of these situations have not been solved. Herein, inventions are disclosed that generate osmotic pressure that can be used to remove these fluids very effectively, a technique which requires no harsh suction or pumping. One embodiment involves implanting a reservoir that has a semipermeable membrane sidewall. The reservoir contains trapped osmotic solutes that can not pass out through the membrane. But fluid from the patient can flow in. The osmotic pressure from the trapped solutes in the reservoir draws fluid from the patient across the semipermeable membrane and into the device. In some versions, the membrane can be changed as desired during the lifetime of the device by pulling the membrane out through the implanted device and putting a new one back in.

10 Claims, 35 Drawing Sheets

U.S. PATENT DOCUMENTS

| | | | |
|---|---|---|---|
| 5,037,385 A | 8/1991 | O'Byrne | |
| 5,152,757 A * | 10/1992 | Eriksson | 604/305 |
| 5,234,438 A | 8/1993 | Semrad | |
| 5,254,084 A | 10/1993 | Geary | |
| 5,752,939 A | 5/1998 | Makoto | |
| 5,782,841 A | 7/1998 | Ritz et al. | |
| 5,833,654 A | 11/1998 | Powers et al. | |
| 5,885,217 A | 3/1999 | Gisselberg et al. | |
| 5,944,684 A | 8/1999 | Roberts et al. | |
| 5,980,481 A | 11/1999 | Gorsuch | |
| 5,989,216 A | 11/1999 | Johnson et al. | |
| 6,004,326 A | 12/1999 | Castro et al. | |
| 6,030,358 A | 2/2000 | Odland | |
| 6,193,684 B1 | 2/2001 | Burbank et al. | |
| 6,234,991 B1 | 5/2001 | Gorsuch | |
| 6,409,699 B1 | 6/2002 | Ash | |
| 6,537,241 B1 | 3/2003 | Odland | |
| 6,632,192 B2 | 10/2003 | Gorsuch et al. | |
| 6,699,225 B2 | 3/2004 | Fujii | |
| 6,749,580 B2 | 6/2004 | Work et al. | |
| 6,942,633 B2 | 9/2005 | Odland | |
| 6,942,634 B2 | 9/2005 | Odland | |
| 6,997,914 B2 | 2/2006 | Smith et al. | |
| 7,018,384 B2 | 3/2006 | Skakoon | |
| 7,261,705 B2 | 8/2007 | Edoga et al. | |
| 2003/0163079 A1 | 8/2003 | Burnett | |
| 2004/0049288 A1 | 3/2004 | Levin | |
| 2004/0147807 A1 | 7/2004 | Viebach et al. | |
| 2004/0147871 A1 | 7/2004 | Burnett | |
| 2004/0215186 A1 | 10/2004 | Cornelius et al. | |
| 2005/0043673 A1 | 2/2005 | Lieberman | |
| 2005/0192548 A1 | 9/2005 | Dolliver et al. | |
| 2006/0058731 A1 | 3/2006 | Burnett et al. | |
| 2007/0038172 A1 | 2/2007 | Zamierowski | |

FOREIGN PATENT DOCUMENTS

| | | |
|---|---|---|
| WO | 99/07276 A2 | 2/1999 |
| WO | 03/072166 A1 | 9/2003 |
| WO | 2006/020370 A2 | 2/2006 |
| WO | 2006/023589 A2 | 3/2006 |
| WO | 2006/047708 A2 | 5/2006 |
| WO | 2008/092090 A2 | 7/2008 |
| WO | 2008/098207 A2 | 8/2008 |

OTHER PUBLICATIONS

Demissachew et al., "Tissue Sources and Blood Flow Limitations of Osmotic Water Transport Across the Peritoneum", J. Am. Soc. Nephrol., 10:347-353 (1999).

Feher et al., "A Simple Student Laboratory on Osmotic Flow, Osmotic Pressure, and the Reflection Coefficient", Advances in Physiology Education, 13(1):S10-S20 (Jun. 1995).

Flessner, "Peritoneal Transport Physiology: Insights from Basic Research", J Am Soc Nephrol, 2(2):122-135 (1991).

Flessner et al., "Peritoneal Changes after Exposure to Sterile Solutions by Catheter", J. Am. Soc. Nephrol, 18:2294-2302 (2007).

Flesssner et al., "In Vivo Determination of Diffusive Transport Parameters in a Superfused Tissue", Am J Physiol Renal Physiol, pp. 1-31 (May 9, 2006).

Flessner et al., "Similitude of transperitoneal permeability in differnet rodent species", Am J Physiol Renal Physiol, 292:F495-F499 (2007).

Guntheroth, "Decompensated Heart Failure and Diuretic Resistance", JACC, 48(5):1059-1060 (Sep. 5, 2006).

Koso, "A Toolkit: The Management of Lymphedema in Lower Extremities by Subcutaneous Drainage", CarePartners Palliative Care, Apr. 2008, 5 pages.

Lam et al., "Use of closed controlled subcutaneous drainage to manage chronic lower limb oedema in patients with advanced cancer", Hon Kong Med J, 15(1):65-68 (Feb. 2009).

Odland et al., "Effect of tissue ultrafiltration of skip flap survival", Otolaryngology—Head and Neck Surgery, 131 (3):296-299 (Sep. 2004).

Panousis et al., "Suction dressings in total knew arthroplasty—an alternative to deep suction drainage", Acta Orthop. Belg., 70: 349-354 (2004).

Rockson et al, "Estimating the Population Burden of Lymphedema", Ann NY Acad Sci, 1131:147-154 (2008).

Stachowska-Pietka et al., "Distributed model of peritoneal fluid absorption", Am J Physiol Heart Circ Physiol, 291:H1862-H1874 (2006).

Tiwari et al., "Differential Diagnosis, Investigation, and Current Treatment of Lower Limb Lymphedema", Arch Surg, 138:152-161 (Feb. 2003).

Walsh et al., "Intractable Congestive Heart Failure Successfully Treated with Southey Tubes", Canad Med Ass J, 90:1375-1376 (Jun. 13, 1964).

* cited by examiner

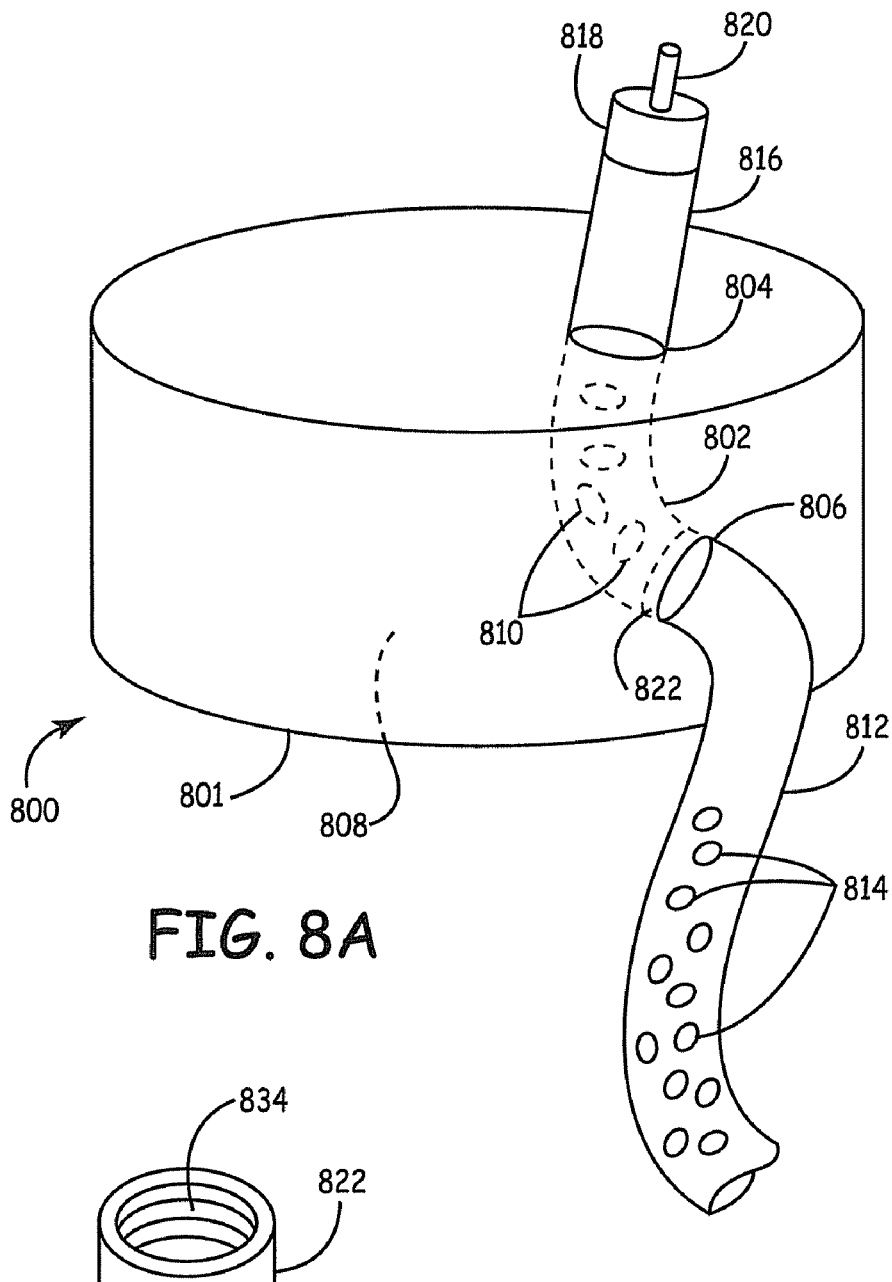
FIG. 8A
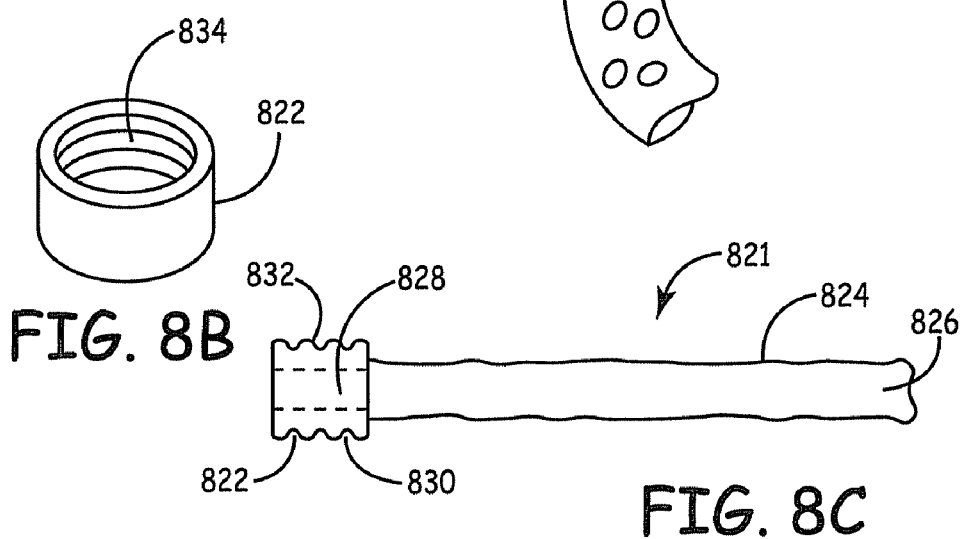
FIG. 8B
FIG. 8C

PRIOR ART SOUTHEY TUBE

PRIOR ART SOUTHEY TUBE

INTEROSMOLAR FLUID REMOVAL

This application claims priority to U.S. provisional patent Ser. Nos. 61/127,440 filed May 13, 2008, and 61/137,921 filed Aug. 5, 2008 which are hereby incorporated by reference herein.

BACKGROUND

Many persons suffer from conditions such as diabetes, edema, congestive heart failure, or ascites. Many therapies exist for these conditions but many unresolved problems remain to be addressed.

SUMMARY

Herein, devices and methods are disclosed that remove fluids very effectively using osmotic pressure and flow, a technique which requires no harsh suction, vacuum, or pumping. One embodiment involves implanting a reservoir that has a semipermeable membrane sidewall. The reservoir contains trapped osmotic solutes that can not pass out through the membrane. But fluid from the patient can flow in. The osmotic pressure from the trapped solutes in the reservoir draws fluid from the patient across the semipermeable membrane and into the device. The fluid is disposed of, or redirected. Very small or very large osmotic pressures can be generated to treat a wide range of situations.

In general, reservoirs and catheters are described herein for removing fluid from a patient or moving fluid from one location to another in the body. These devices include a semipermeable membrane that traps solutes inside the membrane to create an osmotic driving force to pull fluids and other materials below the molecular weight cut-off (MWCO) of the membrane into the device for removal or redirection within the body.

The osmotic pressure that the device creates to drive fluids may be set to be very high. As a result, fluids may be readily moved without resorting to suction, vacuum, compression, or gravity drainage techniques. Applications include, e.g., dialysis, peritoneal dialysis, edema, edema of the limbs, torso, or cranium, pulmonary edema, or ascites.

Some embodiments have an external reservoir that connects to an internal reservoir and/or catheter. The external reservoir is attached permanently or reversibly, or from time to time. The internal reservoir may be a container that collects fluids directly and/or a container that has tubing that collects fluid into the container, with the tubing and container having common fluid communication so that osmotic pressure in the container is shared by the collector-tubing.

Some embodiments have an internal reservoir that collects fluid directly or via tubing that draws fluid into the internal reservoir. The internal reservoir can be percutaneously accessed or have a transcutaneous port for permanent or reversible connection to devices external to the body.

Some embodiments relate to systems for changing-out a fluid collection system. A container or cage is implanted in the patient and the fluid collector is passed into the container/cage and secured to accomplish fluid removal. The collector can also be removed through the collector/cage. One benefit of this approach is that semipermeable membranes on the fluid collector can be changed out from time to time if they become biofouled. In some embodiments, the fluid collector is an insert that seats in an internal-reservoir container and the reservoir and collector share a common solution of trapped osmotic solutes. In some other embodiments, the fluid collector fits into the cage, which provides structural support for the insert but does not help to contain trapped osmotic solutes within the collector.

In other embodiments, the fluid collector has a semipermeable membrane and trapped osmotic solute integrated with a catheter, needle, or other structure to provide a fluid collection system.

Various medical applications for the fluid collection are described.

BRIEF DESCRIPTION OF THE FIGURES

FIG. 8A depicts a reservoir with a pass-through channel;

FIG. 8B depicts the seat of the embodiment of FIG. 8A;

FIG. 8C depicts an insert for passage through the channel and seating in the seat of FIGS. 8A and 8B;

DETAILED DESCRIPTION OF PREFERRED EMBODIMENTS

Figure 1A:
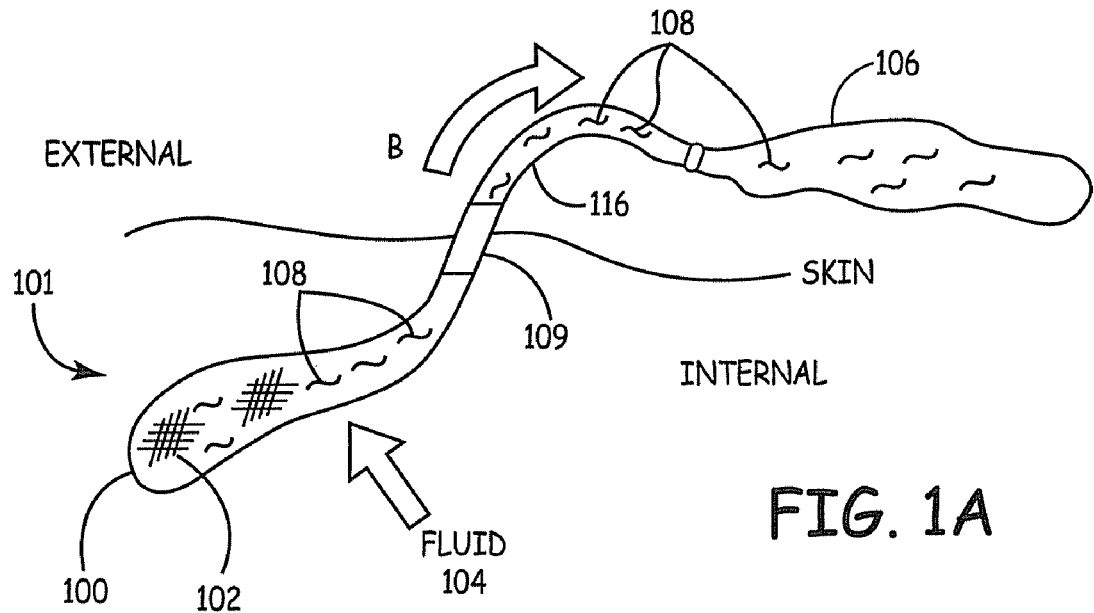
FIG. 1A depicts a semipermeable membrane fluid collection system with an implantable catheter and an external reservoir.

Osmotic pressure may be used to move fluids within, or remove fluids from, a patient. FIG. 1 is a schematic. At FIG. 1A, device 101 has an implanted semipermeable membrane 100 that defines a lumen 102 with trapped osmotic solutes 108 that create osmotic pressure that draws fluid 104 into the lumen. The lumen is in fluid communication with an external reservoir 106 that fills by osmotic pressure, as at arrow B. Transdermal connector 109 connects lumen 102 and reservoir 106. The osmotic pressure is created by the presence of trapped osmotic solutes 108 that can not pass through the semipermeable membrane 100. In use, fluid 104 that passes into the device is drawn off and solutes 108 are replaced as needed to maintain a desired osmotic pressure. Reservoir 106 is elastic and expands as fluid 104 enters the device. Lumen 102 may have a relatively low volume so as to be positionable in a wide variety of bodily spaces, with reservoir 106 having a larger capacity to store fluids. In some embodiments, the lumen 102 is the lumen of a catheter or hollow fiber membrane.

Figure 1B:
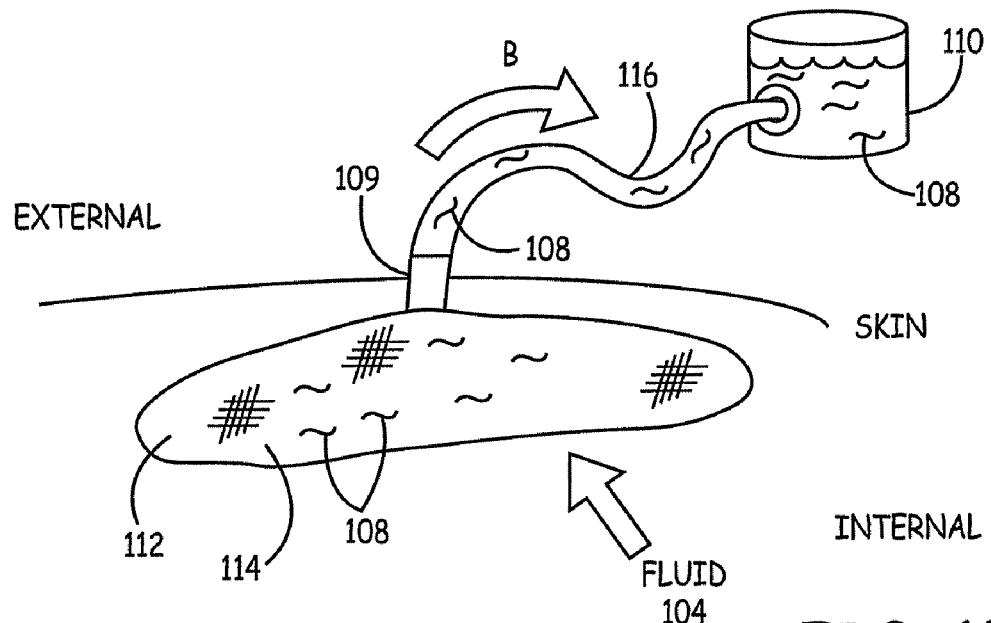
FIG. 1B depicts a semipermeable membrane fluid collection system with an implantable reservoir and an external reservoir.
Figure 1C:
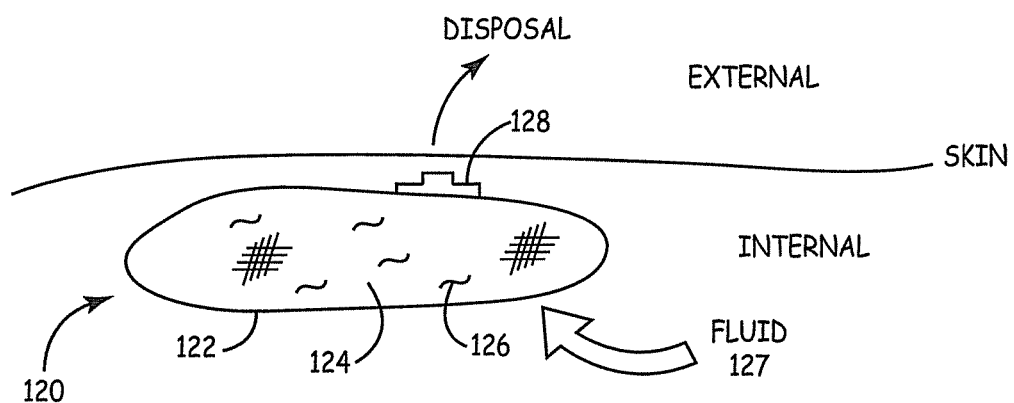
FIG. 1C depicts a semipermeable membrane fluid collection system with an implantable reservoir equipped with a percutaneous access port.
Figure 1D:
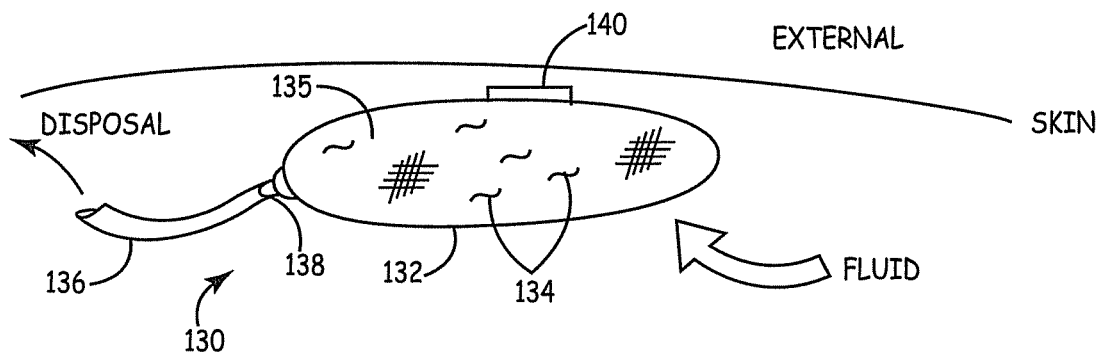
FIG. 1D depicts a semipermeable membrane fluid collection system with an implantable catheter and an external reservoir that redirects fluid from the reservoir for disposal.

Alternatively, a rigid reservoir may be used, as in reservoir 110 in FIG. 1B, which has a semipermeable membrane 112 that defines lumen 114. Fluid, as at arrow B, flows through tubing 116 into reservoir 110 by osmotic pressure. Lumen 114 is relatively larger than lumen 102 and can serve as a temporary depot for fluid storage. Accordingly, reservoir 110 may be intermittently connected to lumen 114. In some embodiments, reservoir 110 is replaced with a device that removes fluid from lumen 114 without reference to osmotic forces, e.g., a catheter at atmospheric pressure or under vacuum, a syringe, or a vacuum pump FIG. 1C depicts implanted device 120 with semipermeable membrane 122 that defines lumen 124 that contains trapped osmotic solutes 126. The device is fully implanted, meaning it has no members that are external to the body. Fluid 127 passes into lumen 124. Port 128 is accessed through the skin, e.g., by a needle and syringe, to remove fluid 128 and replace or supplement solutes 126 as desired. FIG. 1D shows alternative device 130 with semipermeable membrane 132 that contains trapped solutes 134 in lumen 135. Catheter 136 directs fluid out of the device, either to another location in the body (e.g., intraperitoneal space, bladder) or externally to a reservoir or ostomy bag. Optional 1-way valve 138 prevents backflow into lumen 135 and may further have a semipermeable membrane sized to prevent exit of trapped solutes 134 from the device. Optional device 140 may be a push-button or diaphragm or other mechanism to generate internal pressure to force fluid into catheter 136 and/or a fill/drain port for access by a needle and a vacuum device, e.g, syringe, vacuum tube, pump.

To use such a device, a user may implant the device in a patient with ports or catheters, if present, passing through the patient's skin. The device lumen is loaded before or after implantation with fluid that contains trapped osmotic solutes. Native fluids from the patient are drawn into the device by osmosis. The fluids are then redirected or disposed of. Osmotic trapped solutes are internal to the device and can not pass through the semipermeable membrane; the ongoing presence of these solutes contributes osmotic pressure that draws native fluids into the device. The loaded fluid, meaning fluid introduced into the device by a user, may alternatively or additionally have solutes with molecular weights less than the molecular-weight cut-off, referred to as diffusible solutes. Solutes that pass from the subject into the device are diffusible solutes and may be specifically referred to as native diffusible solutes. Similarly, fluids passing into the device are physiological fluids and may be specifically referred to as recovered native fluids; these fluids are water with various diffusible solutes. Native fluid is the fluid present in the patient. Physiological saline is a term for osmotically balanced solutions, and such salines made ex vivo and placed in the device may specifically be referred to as exogenous physiological saline. A solute is a moiety dissolved in a solvent.

In general, this approach may be used to create very powerful forces for moving fluids. The osmotic pressures can be much greater than gravity such that fluids can travel against the force of gravity to flow into the device or out of the device into a reservoir. At the same time, however, osmotic forces rely on the diffusion of water as opposed to suction.

Such devices may be provided in a variety of configurations. Features that may be mixed-and-matched to make a device include, for example: one or more of an external reservoir, an internal reservoir, an appendages for fluid collection, a location of the semipermeable membrane, a fluid removal motif, (percutaneous, internal redirection, transcutaneous port), and a port. FIGS. 1A and 1B depict how the trapped osmotic solutes are distributed in a solvent and in fluid communication throughout the internal portions of the device, with some device portions being inside the patient and some outside the patient. Any shape of the device may be made to accommodate the fluids. Accordingly, reservoir(s) may be used in the device in combination with variously shaped appendages sized and dimensioned as needed for placement in a patient. The term appendage and reservoir are sometimes used to distinguish between portions of the device as it is generally configured for practical use and for the convenience of description; thus a reservoir generally has a volume of more than about 50 ml and an appendage has less than about 50 ml volume. Appendages may be, e.g., from 0.1 ml to about 50 ml in volume; artisans will immediately appreciate that all ranges and values between the explicitly stated values are contemplated, e.g., less than 10 ml, from about 0.2 ml to about 10 ml, or 0.5 ml to about 5 ml. Moreover, some appendages are conveniently shaped for placement by trocar or tunneling and, at the time of placement, are sized to pass through an opening (e.g., a catheter interior, a port, a tunnel in a tissue) with of less than about 1 mm$^2$ to about 200 mm$^2$ cross-sectional area; artisans will immediately appreciate that all ranges and values between the explicitly stated values are contemplated, e.g., 1.5 mm$^2$ or from about 1 to 50 mm$^2$. Examples of appendages are tubes, hollow tube fibers, catheters, ovoids, bags. Reservoirs may be any size, e.g., from about 50 ml to about 10,000 ml; artisans will immediately appreciate that all ranges and values between the explicitly stated values are contemplated, e.g., about 50 ml to about 2000 ml or 100 ml to about 1000 ml.

Figure 2A:
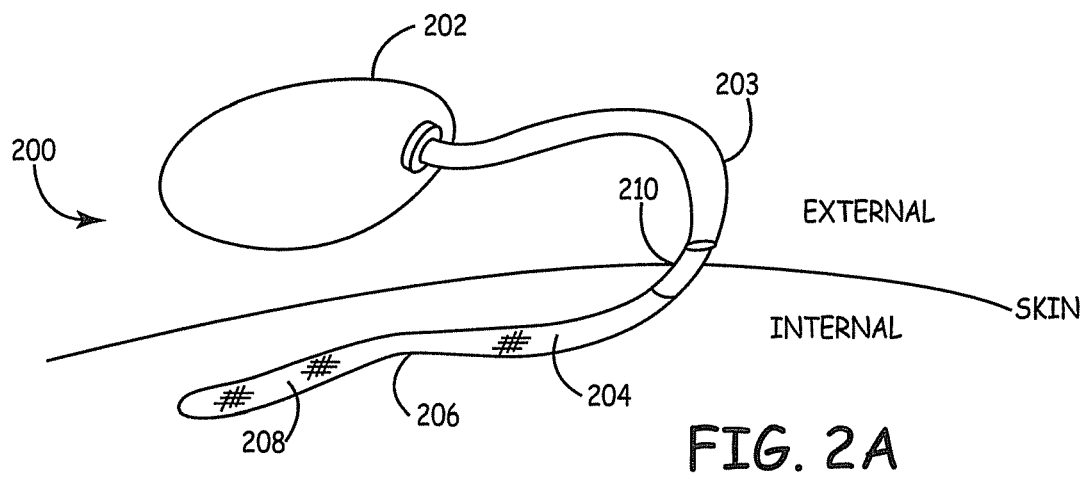
FIG. 2A depicts an alternative semipermeable membrane fluid collection system with an implantable catheter and an external reservoir.
Figure 2B:
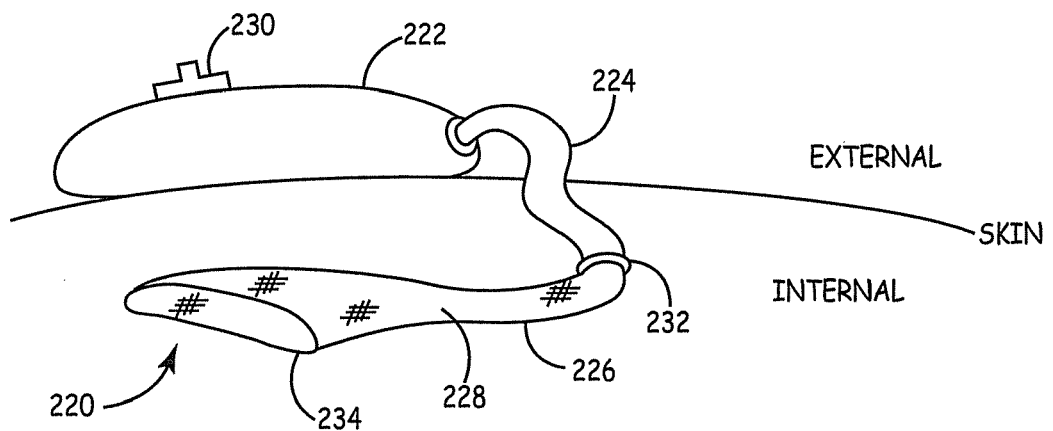
FIG. 2B depicts an alternative semipermeable membrane fluid collection system with an implantable catheter and an external reservoir.

For example, FIG. 2A depicts device 200 having external reservoir 202 in fluid communication via tubing 203 with lumen 204 of appendage 206 that comprises semipermeable membrane 208. Transcutaneous connector 210 links the appendage and reservoir. Tubing 203 may be reversibly or permanently connected to connector 210. Appendage 206, as depicted, is not a reservoir, but has an elongated and narrow shape for ease of placement, e.g., a tubular shape with a maximum diameter of about 5 mm. And FIG. 2B depicts a device 220 with reservoir 222, tubing 224, appendage 226 having lumen 228 and semipermeable membrane 228. A fill/drain port 230 is provided for the external reservoir 222. Appendage 206 is relatively narrow at connection 232 and expands distally to terminus 234.

FIG. 3 depicts further examples of said mixed-and-matched features. Device 300 has reservoir 301 with a top side 302 connected to a bottom side 306 by a side 304 that each comprises a semipermeable membrane. Fill/drain port 308 allows access to reservoir 301. Reservoir 301 is implanted in a patient with port 308 being fully internal to the patient for percutaneous access or extending transcutaneously through the patient's skin for external access. Native fluid has access to the reservoir from all sides 302, 304, 306. FIG. 3C depicts a device 310 with semipermeable membrane disposed only at its peripheral edges 312. Top portion 314 and bottom portion (not shown) are not permeable. Fill/drain port 316 allows access to reservoir 311. FIG. 3D is an alternative embodiment of FIG. 3C, with device 313 having an intradermal skin cuff 318 on fill/drain port 316.

Figure 3A:
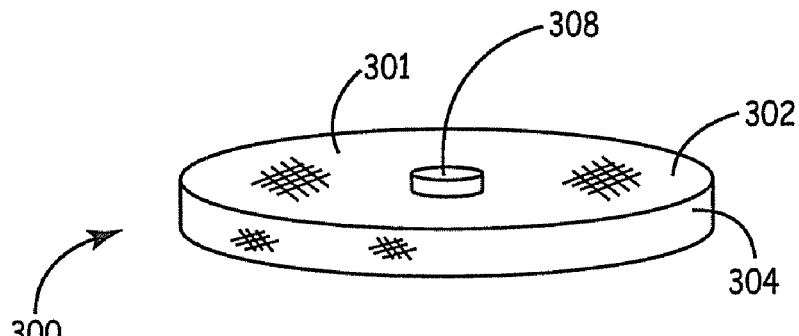
FIG. 3A is a perspective view of an implantable fluid collection reservoir bounded by a semipermeable membrane on all its faces.
Figure 3B:
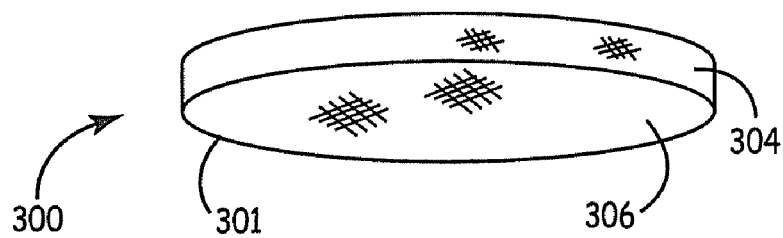
FIG. 3B is a bottom perspective view of the embodiment of FIG. 3A.
Figure 3C:
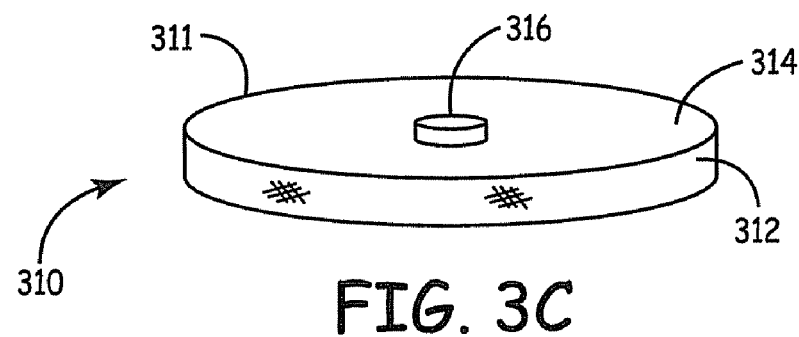
FIG. 3C is a perspective view of an implantable fluid collection reservoir with a lumen partially bounded by a semipermeable membrane.
Figure 3D:
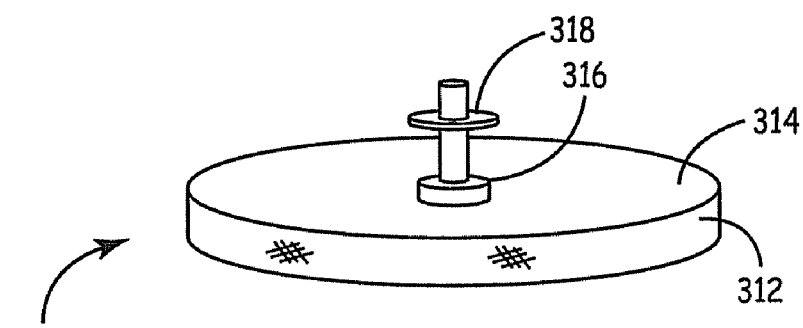
FIG. 3D is a perspective view of the embodiment of FIG. 3C with the access port furnished with a cuff for a transcutaneous application.
Figure 3E:
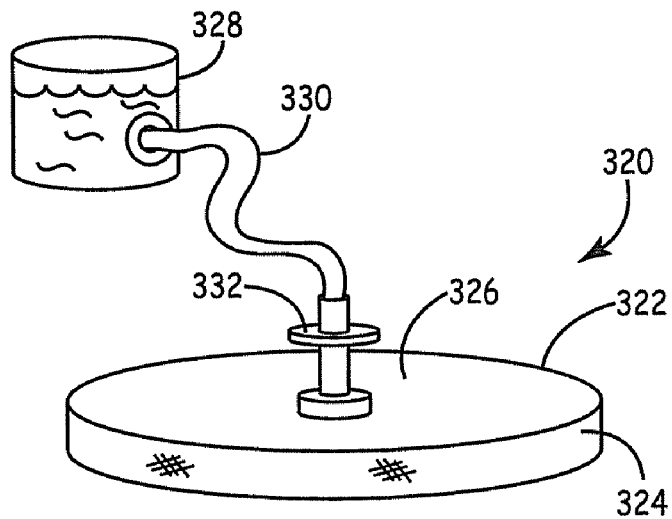
FIG. 3E depicts a fluid collection system with an implantable reservoir fluidly connected to an external rigid reservoir.

FIG. 3E depicts device 320 having internal reservoir 322 that has semipermeable membrane disposed on its edge 324 and bottom (not shown) but not on its top 326. Lumen of reservoir 322 is in fluid communication with external rigid reservoir 328 via tubing 330 and transcutaneous port 332. Tubing 330 is reversibly connectable to port 332 for convenient refreshing of reservoir 322.

Figure 3F:
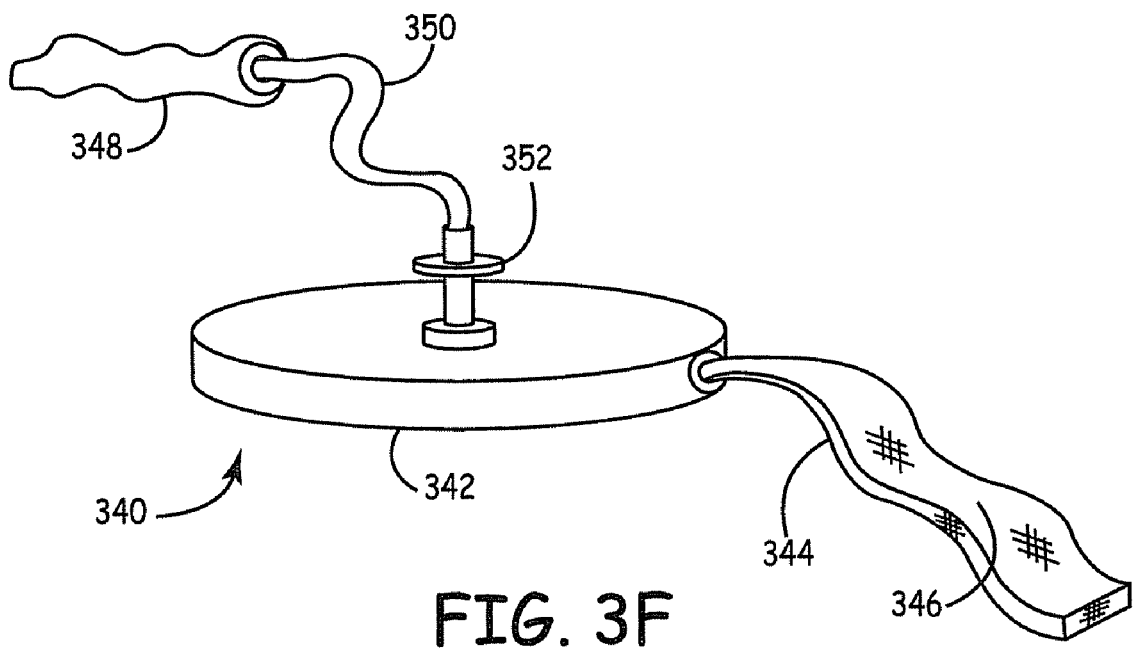
FIG. 3F depicts a fluid collection system with an implantable impermeable reservoir with a semipermeable appendage in combination with an external expandable reservoir.

FIG. 3F depicts device 340 having internally implanted reservoir 342 that is made of non-water-permeable materials that is in fluid communication with a lumen of appendage 344 that is comprised of a semipermeable material. External reservoir 348 (which expands under pressure as fluid enters the device) is in fluid communication with reservoir 342 via tubing 350 and port 352.

Figure 3G:
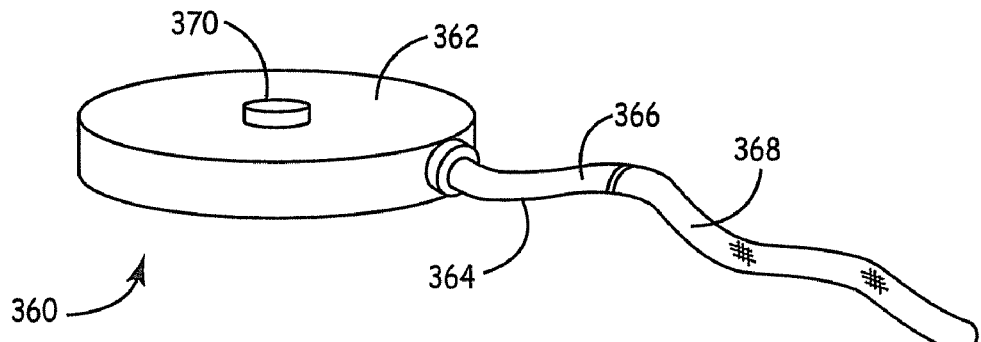
FIG. 3G is a perspective view of a fluid collection system with an impermeable reservoir and a catheter with a distal portion having a semipermeable membrane for passage of native fluids into the device.

FIG. 3G depicts device 360 with non-water-permeable reservoir 362 connected to appendage 364, which has a non-water-permeable portion 366 that is continuous with semipermeable membrane portion 368. The reservoir 362 may be fully implantable with port serving as a percutaneous fill/drain port or reservoir 363 may be external, with nonpermeable portion 366 being transcutaneous.

Figure 3H:
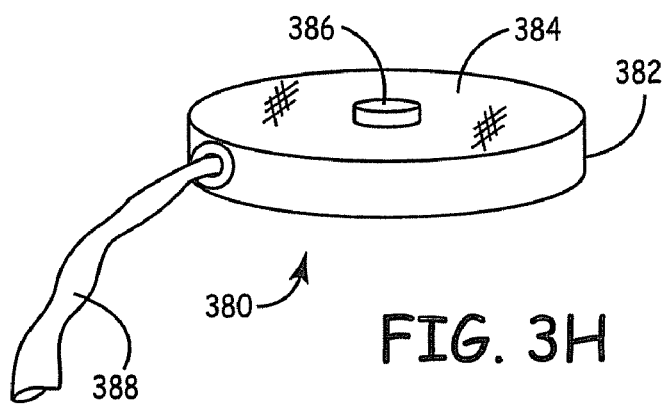
FIG. 3H is a perspective view of a fluid collection system with an reservoir at least partially bounded by a semipermeable membrane and a catheter for redirecting fluid out of the device.

FIG. 3H depicts device 380 with fully implantable reservoir 382 having a semipermeable membrane portion 384 and port 386. Tubing 388 is used for redirecting fluid from reservoir 382 to other portions of the body, or externally through the skin to a collector.

Figure 3I:
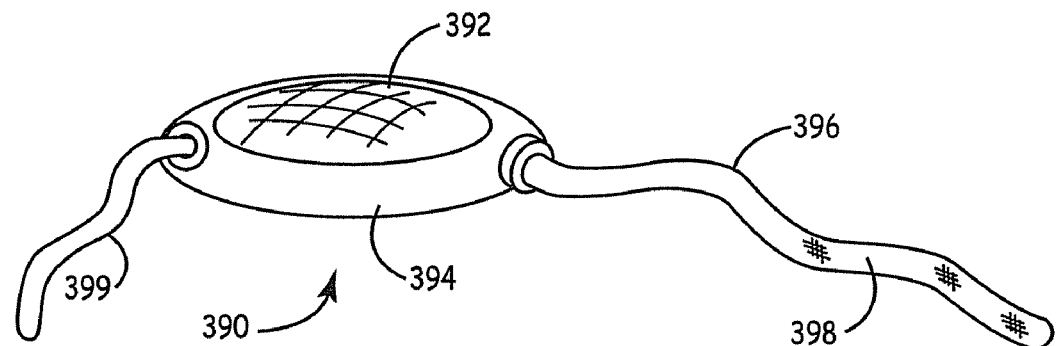
FIG. 3I is a perspective view of a fluid collection system with an appendage having a semipermeable portion and a reservoir having a device for manually forcing fluid out of the collection system and a catheter for redirecting the fluid.

FIG. 3I depicts device 390 that is disc-shaped with a flexible diaphragm portion 392 on reservoir 394, which also has appendage 396 that is tube-shaped with semipermeable membrane portion 398 at its distal segment. Tube 399 is used for redirecting fluid from reservoir 382 to other portions of the body, or externally through the skin to a collector. A user presses on the diaphragm to reduce the interior volume of the reservoir to create pressure to drive fluid out of the reservoir. The appendage 396 may also have a one-way valve to prevent backflow of fluids from the reservoir into the appendage. Tube 399 may also have a one-way valve for preventing backflow into the reservoir, and may also have a filter for retraining trapped osmotic solutes in the reservoir.

In general, a user may implant a device in patient with a semipermeable membrane portion being disposed inside the patient. The device interior is loaded before or after implantation with fluid. The fluid may have trapped solutes having a molecular weight equal to or greater than the molecular weight cut-off of the semipermeable membrane. The fluid may alternatively or additionally have solutes with molecular weights less than the molecular-weight cut-off (diffusible solutes). A solute is a moiety dissolved in a solvent. Thus some embodiments include a lumen at least partially bounded by a semipermeable membrane, meaning that there is a structure that has a lumen (a bore or cavity) with the semipermeable membrane being part of the structure around the lumen. For instance a tube with a sidewall that comprises a semipermeable membrane has a lumen partially bounded by the membrane. Or a container with one or more walls being made of a semipermeable membrane has a lumen at least partially bounded by the membrane. The lumen may be in fluid communication with other specified portions of the device, meaning that trapped osmotic solutes in the lumen may diffuse with or through the solvent to the other specified portions. Thus a lumen in fluid communication with a bore or catheter provides for diffusion of trapped osmotic solutes to the bore or catheter as well as movement of the solvent for the solutes. While a semipermeable membrane does allow fluids to pass, the term "fluid communication" is not used in that sense herein. The term "diffusible fluidic communication" may be used to specifically indicate diffusive/osmotic flow across a semipermeable membrane.

Osmotic solutes in a fluid removal device may include synthetic molecules. Synthetic refers to a molecule not naturally found in a human body. Some osmotic solutes may be synthetic hydrophilic polymers. Hydrophilic refers to a material that has a solubility in water of at least 1 gram per liter. Examples of such polymers are polyethylene glycols (PEG) and polylysines. Natural or synthetic polymers may be used, e.g., polyamino acids such as proteins, polysaccharides, or glycosaminoglycans. Some osmotic solutes are neutral while others are charged to increase ionic attraction and osmolarity. Further exemplary solutes are polyacrylic acid, polyethyleneimine, xanthum gum, sorbates, hyaluronic acid, polyvinyl pyrrolidone, polyacrylamide, polyvinyl alcohol, polyesters.

Trapped osmotic solutes may be present in a fluid collection device according to the molecular weight (MW) of the solute, which relates to the molecular weight cut-off (MWCO) of the semipermeable membrane. Table 1 shows some combinations for MWCO from 100-10,000 with solute MW ranging from 200-12000. The osmotic pressure available to drive fluids is very high. Typical human blood pressure is about 125 Torr or mm Hg (2.4 psi). The inside and the outside of the semipermeable membrane can be expected to approximately equilibrate with respect to the salt content of physiological fluids, such that bodily salt effects on osmotic pressure across the semipermeable membrane of the device may be negligible. The solubility of a 4000 MW PEG in water at room temperature is about 50%, so high concentrations of PEG, for instance, are available as a solute to drive osmosis. Table 1 shows that osmotic driving pressures of more than 60× physiological blood pressure can be generated. MWCOs of more than 10,000 may be used, e.g., MWCO from 12,0000 to 100,000; artisans will immediately appreciate that all the ranges and values within the explicitly stated ranges are contemplated, e.g., about 12,000, about 15,000, about 45,000 or between about 12,000 and about 60,000. As is evident from this disclosure, a trapped osmotic solute may be used at a concentration to generate an osmotic pressure of more than 50,000 Torr or a very low pressure, e.g., 1 Torr; artisans will immediately appreciate that all the ranges and values within the explicitly stated ranges are contemplated, e.g., 1 to 50,000 Torr, 10 to 10,000 Torr, 10 to 5,000 Torr, 10 to 1,000 Torr, 1 to 125 Torr, 5 to 250 Torr, at least 2 Torr, 1,000 to 50,000 Torr, 2,000 to 20,000 Torr, 3,000 to 10,000 Torr. While some of these pressure are quite high, resort may be had to high-strength steel and ceramic materials formed with the desired MWCO. As is evident from this disclosure, a trapped osmotic solute may be used at a concentration as needed to generate a predetermined osmotic pressure or pressure range, e.g., from 0.1 to 10,000 mM; artisans will immediately appreciate that all the ranges and values within the explicitly stated ranges are contemplated, e.g., 2 to 5000 mM, 4 to 2500 mM, at least 2 mM, less than 10,000 mM, 1 to 1000 mM, 50 to 5825 mM. Moreover, the disclosed MWCO, solute MWs and pressures may be mixed-and-matched in combination with each other as appropriate, bearing in mind that selecting one affects choices available for the other two, as is evident.

TABLE 1

| Polymer Solute Molecular Weight | Semipermeable Membrane MWCO | Polymer Solute Concentration, mM or (mg/ml). | Pressure, Torr or (psi) at 37 C. or as indicated. |
| --- | --- | --- | --- |
| 200 | 100 | 2500 (500) | 63.6 atmospheres |
| 600 | 500 | 833 (500) | 21.2 atmospheres |
| 1200 | 1000 | 400 (500) | 7828 (151) |
| 1200 | 1000 | 40 (50) | 782 (15) |
| 6000 | 5000 | 8 (50) | 152 (2.9) |
| 12000 | 10000 | 4 (50) | 76 (1.5) |

Semipermeable materials may be made with a molecular weight cut-off, e.g., from about 50 to about 200,000 molecular weight; artisans will immediately appreciate that all ranges and values between the explicitly stated values are contemplated, e.g., with a range from about 100 to about 10,000, from about 500 to about 5,000, less than 40,000, or less than about 1,000, less than about 2,000, from about 200 to about 4,000, from about 1,000 to about 50,000, or from about 2,000 to about 70,000. The term membrane, as in a semipermeable membrane, is used broadly to refer to a membrane or other solid porous and permeable structure with a MWCO. Processes for making materials with a particular molecular weight cut-off are known in the arts of dialysis and reverse osmosis. Options for such materials include, for example, membranes, plates, and hollow tube fibers. Processes for making such materials include, for example, spin-casting, sintering, and laser perforation. Materials include, for example, ceramics, celluloses, cellophanes, regenerated cellulose, cellulose ester (CE), and polyvinylidene difluoride (PVDF), nanoporous alumina, polysulfone, and cellulose triacetate, or polytetrafluoroethylene (PTFE). The term nonpermeable material refers to a material that does not normally allow passage of an aqueous fluid therethrough under atmospheric pressure and at room temperature.

Figure 4A:
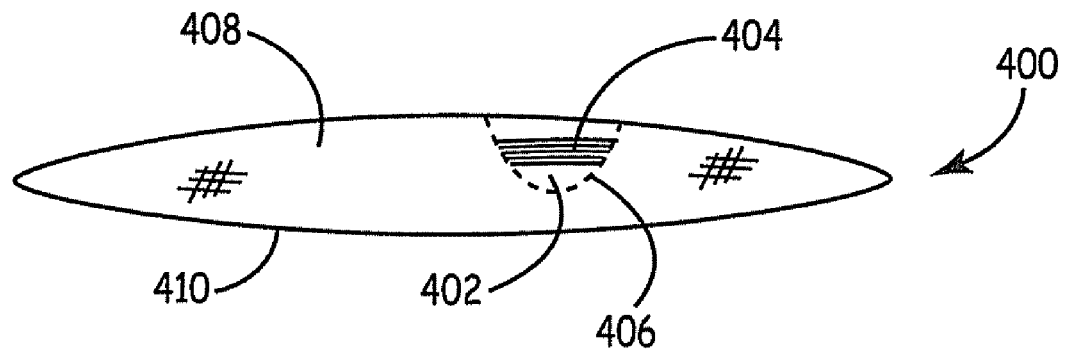
FIG. 4A is a cross-sectional view of a fluid collection device having a semipermeable membrane and an access port.
Figure 4B:
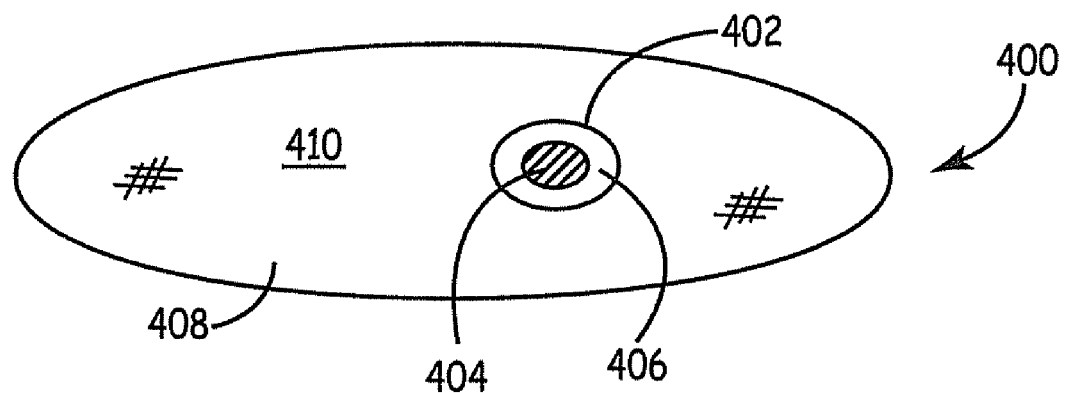
FIG. 4B is a top view of the embodiment of FIG. 4A.

Fluid ports that allow for introduction of fluids in or out of the body may generally be used, e.g., as in U.S. Pat. No. 4,892,518, U.S. Pat. No. 5,833,654, U.S. Pat. No. 5,989,216, U.S. Pat. No. 6,699,225, U.S. Pat. No. 6,997,914, or U.S. Pat. No. 7,261,705. FIG. 4 depicts device 400. In this embodiment, the device 400 has an internal fluidic port 402 with septum 404 over permeable portion 406 that communicates with reservoir 408 having semipermeable portion 410. Device 400 may be implanted inside a person and osmotic solutes internal to reservoir 408 draw native fluids into reservoir 408 through one or more semipermeable portions 410. Users access port 402 with a syringe needle to pierce the patient's skin and self-sealing septum 404 to draw fluids in and out of the device. Port 406 is made of sturdy materials that are not pierced by the needle, e.g., ceramics or certain engineering plastics. Thus the port comprises a backstop (also termed a guard) that allows users to push needles or other devices into the port without fear of damaging the underlying device because the backstop will catch the needle or other object. Permeable portion 406 allows fluids to flow in and out of the reservoir and port. Optional tubing and valves (not depicted) may also be used to move the fluid to other portions of the body or, in a partially implantable version, out through the body to an ostomy bag or other collector. Or a pump may be used, e.g., as in US Pub. No. 2004/014787.

Embodiments include use of an adjustable flow control valve in which the resistance properties of the valve can be changed non-invasively by the user or caregiver. Specifically, for example, a valve designed to minimize overdrainage of a first fluid and maintain intraventricular pressure (IVP) within a normal physiologic range, regardless of patient position may be adapted after reading this application, for instance, a PS MEDICAL STRATA valve. The normally closed DELTA chamber mechanism opens in response to positive pressure. Working with the ball and spring valve mechanism, overdrainage is minimized by utilizing the principle of hydrodynamic leverage. The DELTA chamber designed by Medtronic provides The Medtronic PS MEDICAL DELTA chamber has two silicone elastomer diaphragms, lying flat against two base outlet ports. Fluid flowing from a positive pressure side pushes the diaphragm surfaces away from the outlet ports, allowing fluid to flow through the ports and out the distal tubing. In the DELTA chamber, the inlet area of the diaphragms acted on by fluid flowing under pressure is 20 times greater than the outlet area of the diaphragms acted on by negative hydrostatic pressure or atmospheric pressure from the distal tuning. The normally closed DELTA chamber mechanism opens in response to positive pressure. Accordingly, such a valve may be associated with a housing, reservoir, or tubing of a fluid removal device described herein.

In general, a fluid collection device is configured to capture native fluids for removal, with the native fluids being gathered into the device by osmotic pressure although diffusion in and out of the device does occur. This configuration is distinct from osmotic pumps or other devices that operate by using osmotic pressure to drive a piston or valve or release solutes from the device, with the native fluids ultimately being retained without removal from the device, or with the device being unsuited to periodic removal of the fluids. Another aspect is that the physiological fluids may pass into the device through a semipermeable membrane and are removed from the interior of the reservoir or the device generally, in contrast to devices that require release of solutes and removal of fluid from locations external to the device or a reservoir joined to the device.

A semipermeable membrane surface area may be sized to achieve a desired flow rate in light of its interior osmotic pressure and site of implantation for the particular application. A projected surface area is a projection of the surface area onto a flat surface from three-dimensional space and does not account for roughness or corrugations in the surface that increase the actual surface area. Exemplary ranges for the projected surface area or surface area are from about 1 cm$^2$ to about 10,000 cm$^2$; artisans will immediately appreciate that all ranges and values between the explicitly stated values are contemplated, e.g., about 100 to about 1000 cm$^2$, from about 200 to about 5,000 cm$^2$, or at least about 500 cm$^2$.

In some embodiments, the reservoirs may be loaded with diffusible solutes that are intended to be released from the device. For instance, therapeutic agents may be introduced into the device, e.g., into an internal or external reservoir or catheter. Such agents may include, for example, drugs, diagnostics, or imaging agents. Examples are anti-inflammatory agents, antibiotics, antimitotics, antimicrobials, antifungals, immunosuppressants, preservatives, or imaging agents, e.g., directly visible agents such as dyes, or indirectly visible imaging agents that require mediation of a machine for visualization, as in radiocontrast or MRI agents.

Loaded fluids may be changed from time to time, e.g., by removing substantially all loaded fluids from a device or by changing out a portion of the device that contains the loaded fluids. For instance, loaded fluids may be changed out in a device that has a reservoir and appendage by replacing the reservoir, at least partially emptying the reservoir, or emptying the reservoir and replacing the removed fluids. The frequency of the changes may be periodic, intermittent, or as-desired. For example, hourly, daily, twice daily, twice a week, once a week, and bi-weekly are all options. Or replacement upon collection of a certain volume may be performed, e.g., 0.05 to 5 liters; artisans will immediately appreciate that all ranges and values between the explicitly stated values are contemplated, e.g., 250 ml, 200 to 1000 ml, and so forth.

Figure 5A:
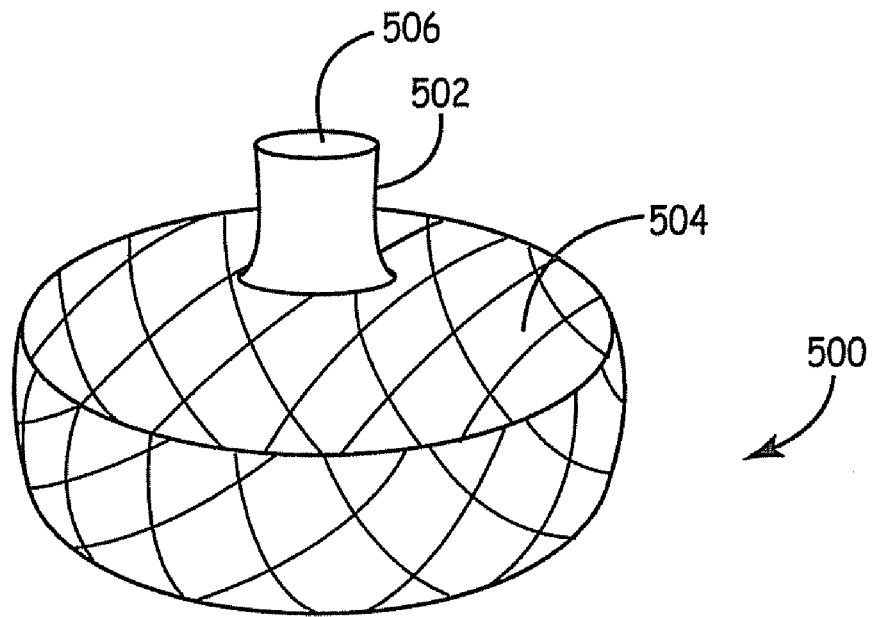
FIG. 5A is a perspective view of an implantable cage.
Figure 5B:
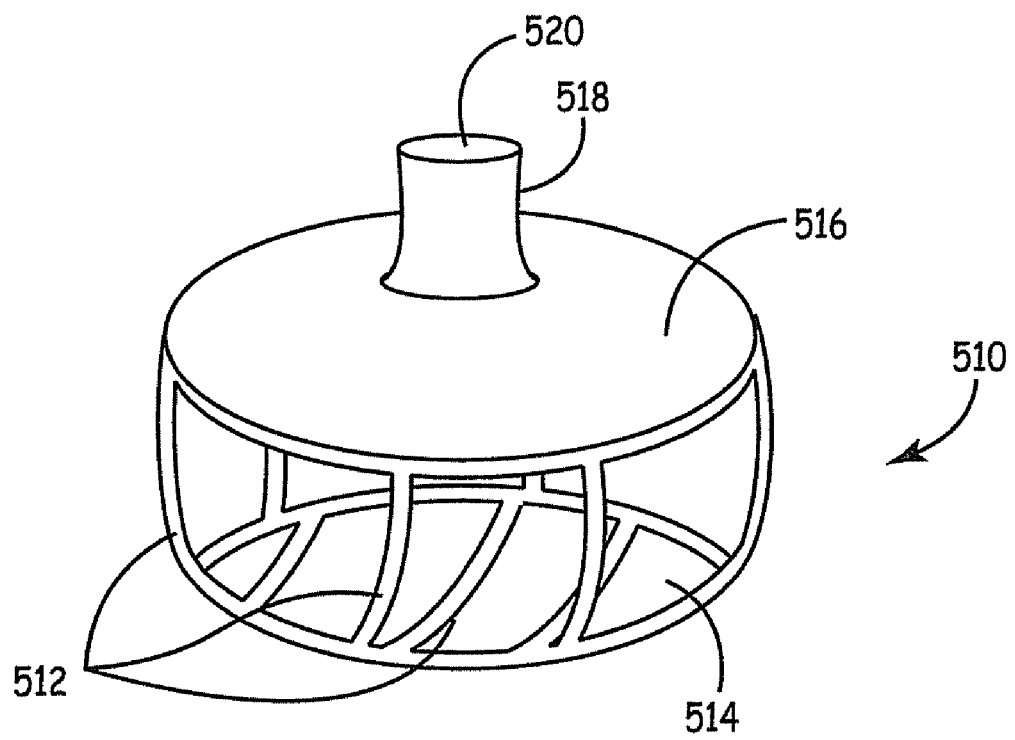
FIG. 5B is a perspective view of an implantable cage.

Other embodiments provide for a cage to hold a reservoir and/or appendage. The cage is implanted and allows materials to pass freely in and out of the cage; no molecular weight cut-off is provided. A structure that comprises a lumen at least partially defined by a semipermeable membrane is inside the cage, either at the time of implantation, introduced afterwards, or removed and replaced after implantation of the cage. FIG. 5A depicts cage 500 with access 502. The cage is at least partially made of a mesh 504 and has an interior space (not depicted) accessible through opening 506. FIG. 5B depicts an alternative embodiment 510 with a series of structural members 512 that collectively define interior space 514. A portion 516 is not permeable. Access 518 has opening 520 that allows access to interior space 514.

Figure 6A:
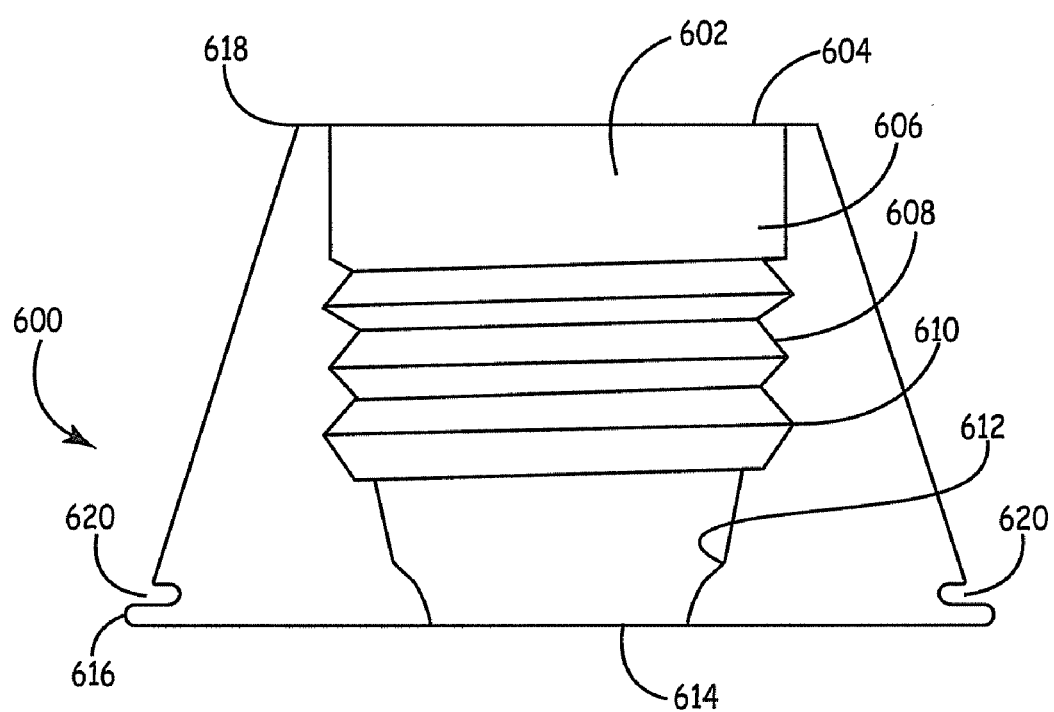
FIG. 6A is a cross-sectional view of a port that provides for passage of devices therethrough and includes a seat and fastener for a device.
Figure 6B:
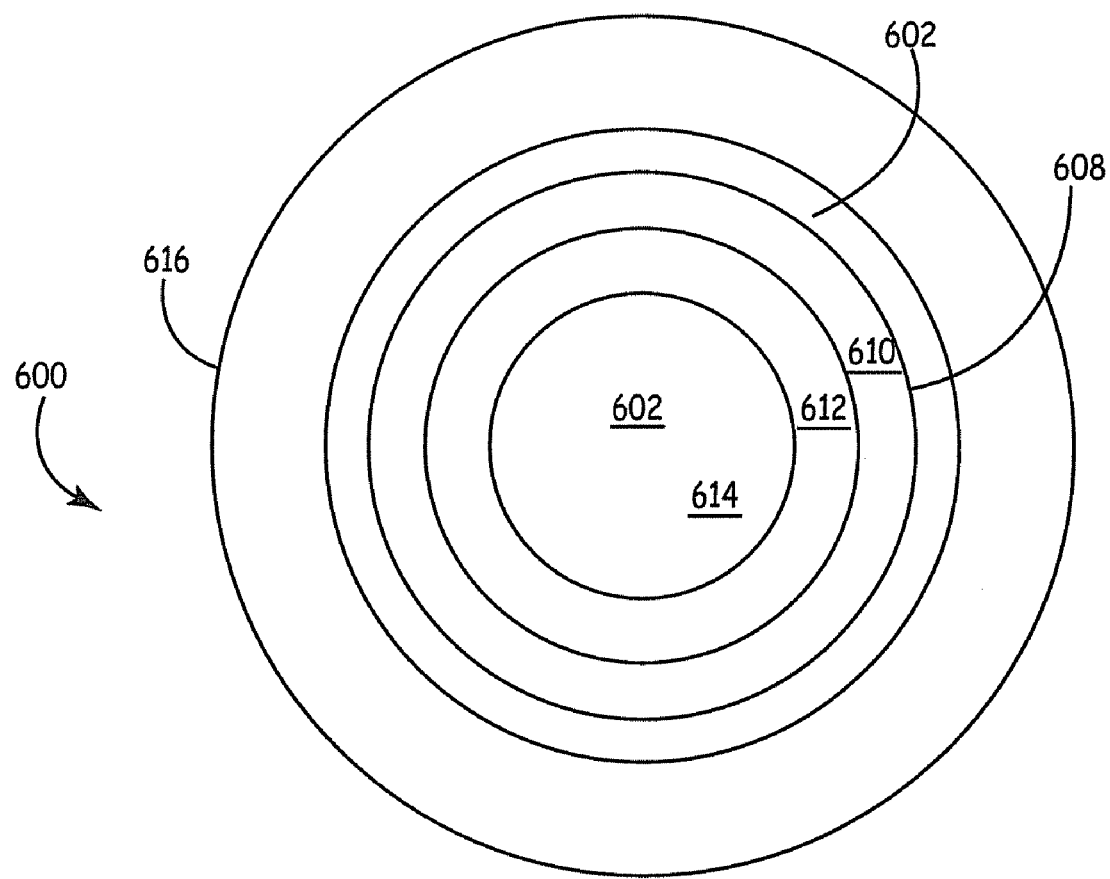
FIG. 6B is a top view of the embodiment of FIG. 6A.

FIG. 6A (cross-sectional elevated view) and FIG. 6B (top plan view) depict an embodiment for an access port, e.g, as in access 502 or 518 of FIG. 5. The access port allows for pass-though placement and/or retrieval of a device that comprises a semipermeable membrane. Such a port may be used in combination with other embodiments described herein. For instance, an implantable reservoir may comprise an access so that semipermeable membranes or other devices may pass through it. The access port 600 has a bore 602 that passes through the device. Bore 602 has inlet 604, proximal portion 606 that comprises fasteners (e.g., threads 608), lip 610, stop 612, and outlet 614. Access port 600 has base 616 that tapers to top 618, with groove 620 for receiving a structure to anchor base 616, e.g, a cage or a semipermeable membrane. In use, a user passes a catheter through inlet 604 until it stops on lip 610 and pushes a device through the catheter and through port 600. Such a device may have a flange that mates with stop 612 such that another (e.g., threaded) fastener may be secured over the flange by engaging the fastener in bore 602, i.e., in this example, threads 608.

Figure 7A:
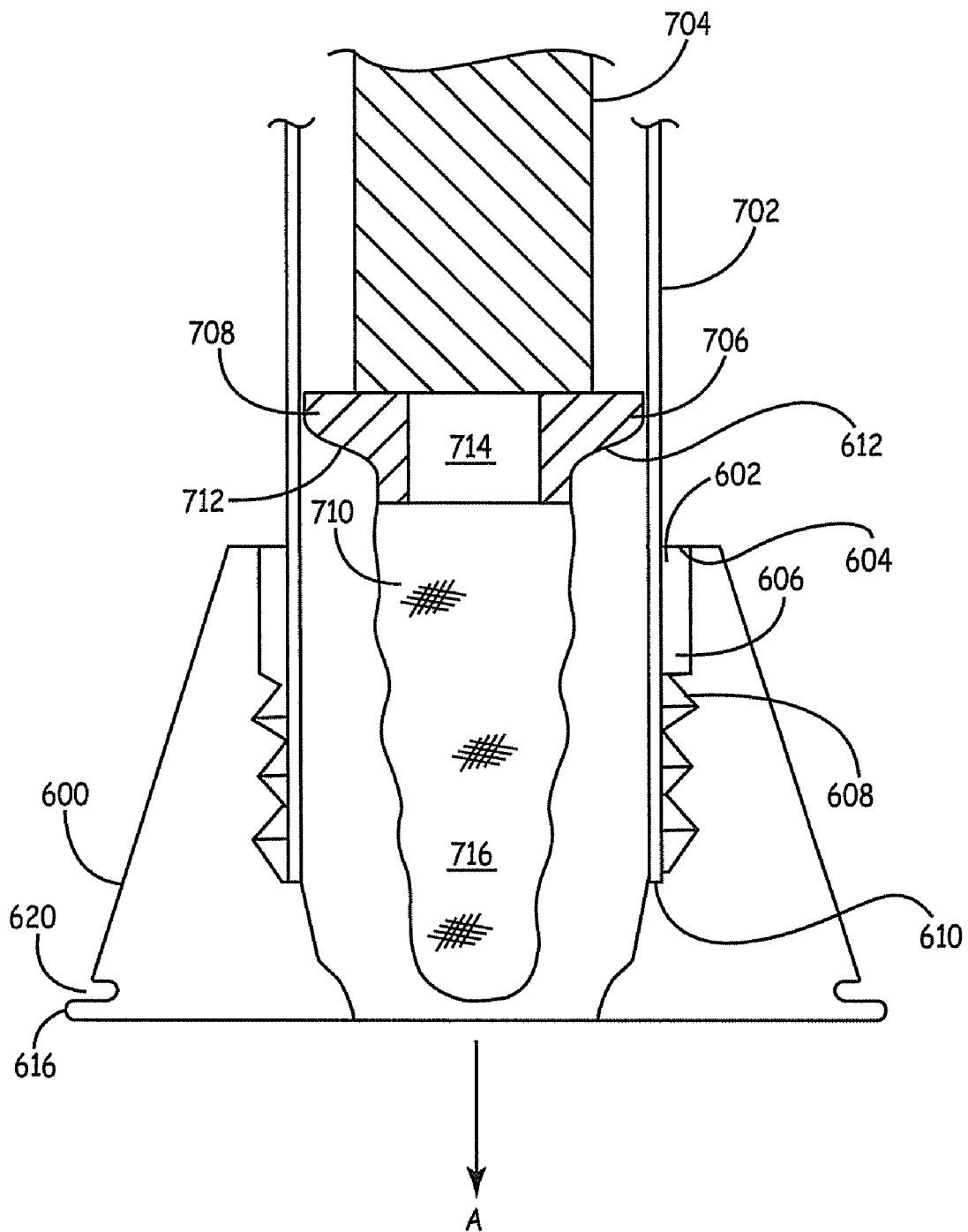
FIG. 7A depicts introduction of a fluid collection device through the embodiment of FIG. 6A.
Figure 7B:
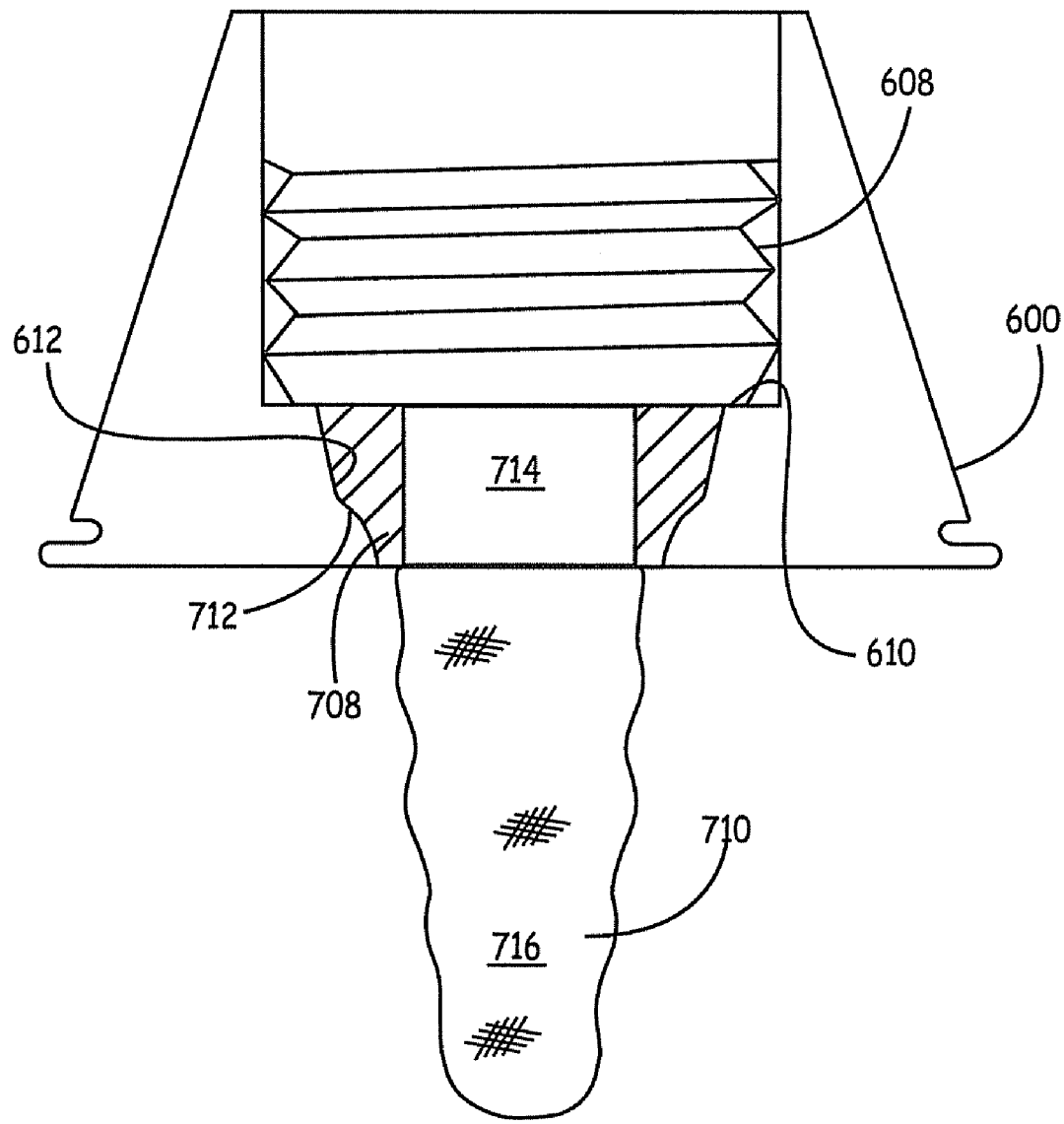
FIG. 7B depicts the device of FIG. 7A being seated in the embodiment of FIG. 6A.
Figure 7C:
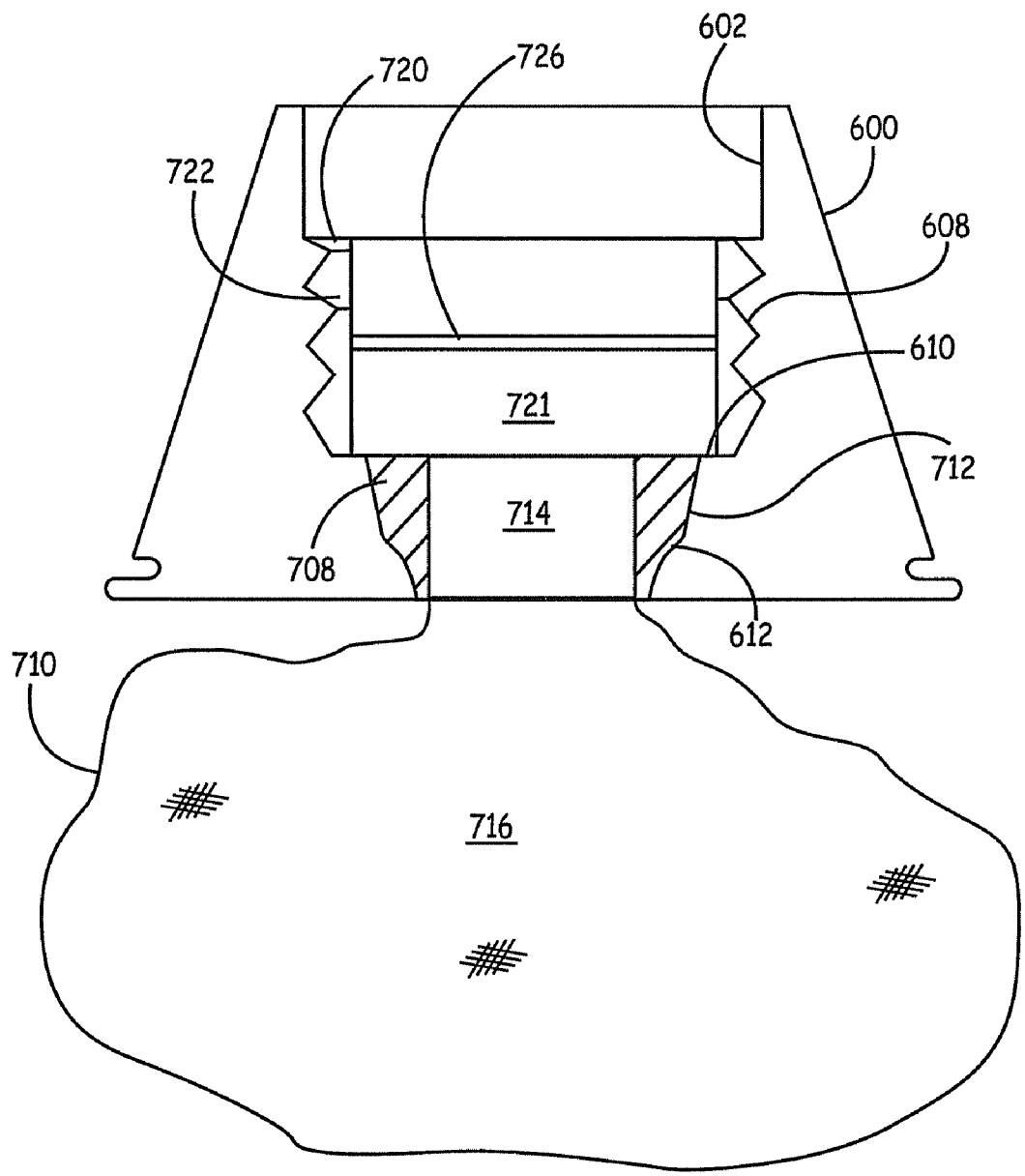
FIG. 7C depicts the embodiment of FIG. 7B with the fluid collection device in an expanded position.

FIG. 7 shows a specific example of a use of port 600. A catheter 702 is passed through inlet 604 and forced against lip 610. A pusher 704 pushes fluid collector 706 through catheter 702 and through bore 602 as indicated by arrow A. Fluid collector 706 has collar 708 joined to semipermeable membrane 710. Collar 708 has mating flange 712 and bore 714. Semipermeable membrane 710 has a lumen 716 that is connected to bore 714. Collector 706 is pushed until mating flange 712 rests securely against flange 612. Catheter 702 and pusher 704 are withdrawn. Bored securing fastener 720 with bore 721 is fastened inside bore 602 to secure collar 708 in port 600, e.g., by engaging threads 722 of fastener 720 with threads 608 of port 600. FIG. 7C shows securing fastener 720 with optional semipermeable membrane 726. Alternatively, a septum (not shown) may be used in the place of membrane 726 or placed above securing fastener 720. The septum may provide for repeated access and resealing, e.g., as in a resilient material that closes after perforation by a needle. Flanges 612 and 712 mate to provide a seal. As is evident, alternative fasteners (e.g., LUER-LOK, friction fit, mortise-and-tenon, tongue-and-groove, compression fit, O-ring seals) may be used and/or flanges 612, 712 may have an arcuate shape as depicted to ease passage of materials or other conformations. Membrane 710 is located within a patient after placement and may be provided before and/or after placement with trapped osmotic solutes to drive collection of fluids into lumen 716. The fluids may be removed as desired through bores 721 and 602, e.g., suction, syringe, gravity, or fluid connection to a reservoir with trapped osmotic solutes. Port 600 is adaptable to, among other things, (internal or external) reservoirs and/or (internal or external) catheters.

In the case of an access port, e.g., port 600, used in combination with a cage, e.g., cage 500 or 510, the port is attached to the cage with its bore in communication with the cage's interior. The cage may be placed inside a patient and a fluid collection device comprising a semipermeable membrane that contains trapped osmotic solutes is placed inside the cage. Fluids pass freely through the cage and into the fluid collection device. The fluids are then redirected or removed from the patient. The fluid collection device may be retrieved and replaced as desired through the access port. Grooves or indents may further be provided on the fluid collection device to facilitate retrieval. For instance, a tool with ears or a ring is introduced into bore 714 after removal of securing fastener 720 and engages indents or a groove in collar 708, and a user pulls the fluid collection device out through port 600.

An alternative pass-through system is depicted in FIG. 8. System 800 has reservoir 801 with inlet 804 and outlet 806 connected by interior channel 802. Devices may be passed through the reservoir 801 by passing the devices through the channel 802, which guides the devices from inlet 804 to outlet 806. Channel 802 is in fluid communication with reservoir interior 808, e.g., by holes 810, or other means. In this example, outlet 806 is connected to tubing 812 with perforations 814. Inlet 804 is connected to access port 816 that is connected to connector 818 that comprises fitting 820 for connection to tubing.

One method for using this device is to implant reservoir 801 in the patient and insert fluid collection device 821 through access port 816 and into tubing 812. Device 821 seats in seat 822. Fluid collection device 821 has a semipermeable membrane 824 that at least partially defines lumen 826 which communicates with bore 828 of collar 830, which is attached to membrane 824. Collar 830 has ribs 832 that engage grooves 834 of seat 822. Reservoir 801 and lumen 826 are loaded with osmotic solutes that drive fluids into lumen 826 and reservoir interior 808 for removal via port 816. Reservoir 801 is depicted as a (rigid) cylinder but may be flexible or elastic and any shape, with channel 802 providing enough structural definition to provide for passage of devices therethrough. Membrane 824 may be contained entirely within tubing 812, which may be open-ended or close-ended, or the membrane may pass out of tubing 812. Alternatively, tubing 812 may not be present, with a membrane passing out of reservoir 801 directly into the patient.

A semipermeable membrane may thus be provided in a module that may be removed and replaced through a port in a reservoir. The catheter may also accessible through the port to clean the catheter, e.g., in the case of blockage. For instance, a brush, scraper, or ream may be introduced through the port and passed through the reservoir and through the catheter.

Figures 9A, 9B:
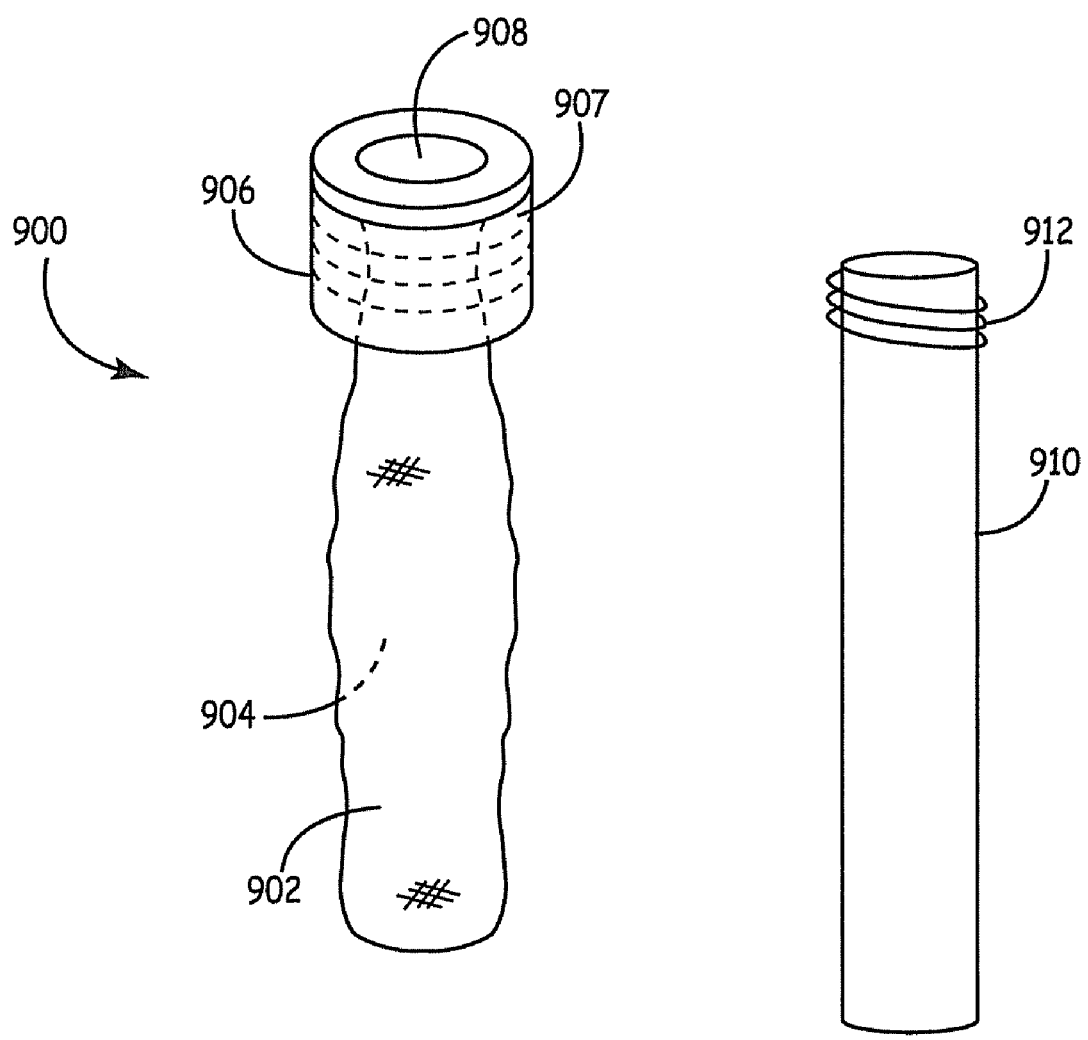
FIG. 9A depicts a fluid collection device with a fastener.
FIG. 9B depicts a catheter with a fastener for use in combination with the embodiment of FIG. 9A.

Another embodiment is a fluid collector that is directly implanted with a suitable port or transcutaneous access, used inside or at least partially inside a catheter, or used in combination with an internal or external reservoir. For instance, FIG. 9A depicts a fluid collector 900 with a semipermeable membrane 902 that at least partially surrounds a lumen 904, with a collar 906 that can receive a port and/or mate with a catheter and/or mate with a reservoir. Collar 906 has bore 908, flange 910 that seals with membrane 902, and threads 907. For instance, catheter 910 (FIG. 9B) has external threads 912 that engage collar threads 907 to secure the collector at least partially inside catheter 910. Alternatively, the embodiment of FIG. 8 may be adapted to receive collector 900, e.g., by substituting male threads at seat 822 or adapting both to another fastening system. A port (not shown) may also engage collar 906 to form a fluid connection, with the port being an access port or connected to other system components.

Figure 9C:
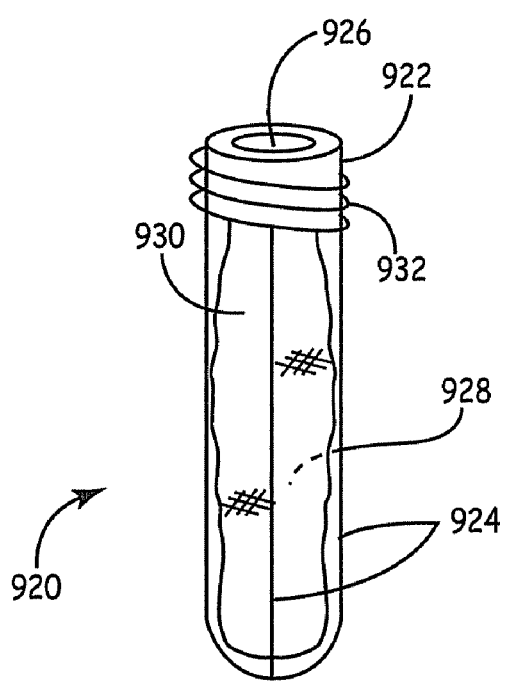
FIG. 9C depicts an alternative embodiment of a fluid collection device that includes a fastener and a cage.

FIG. 9C depicts alternative fluid collector embodiment 920 having collar 922 joined to structural members 924 that serve as a cage, with collar 922 also having bore 926 fluidly connected to lumen 928 surrounded by semipermeable membrane 930. External threads 932 may be used to secure fluid collector 920 in another system component, e.g., a reservoir, tubing, or catheter.

Figure 9D:
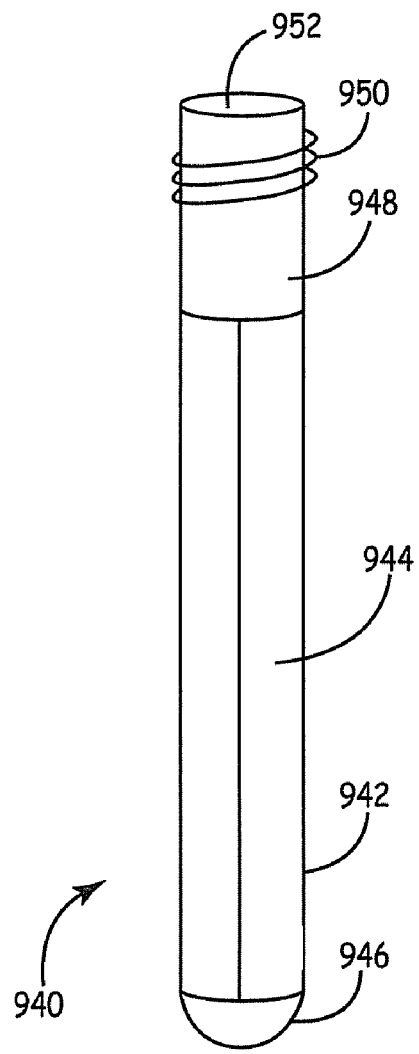
FIG. 9D depicts an alternative embodiment of a cage with a fastener that cooperates with the embodiment of FIG. 9A.

FIG. 9D depicts an alternative catheter 940 with structural members 942 around an otherwise open interior space 944. The structural members 942 are secured to end piece 946 and upper closed portion 948, which has threads 950 and bore 952. Fluid collector 900 may be passed into catheter 940 with semipermeable membrane 902 at least partially disposed in interior space 944. External threads 950 mate with threads 907 to secure collar 906 to catheter 940.

Figure 9E:
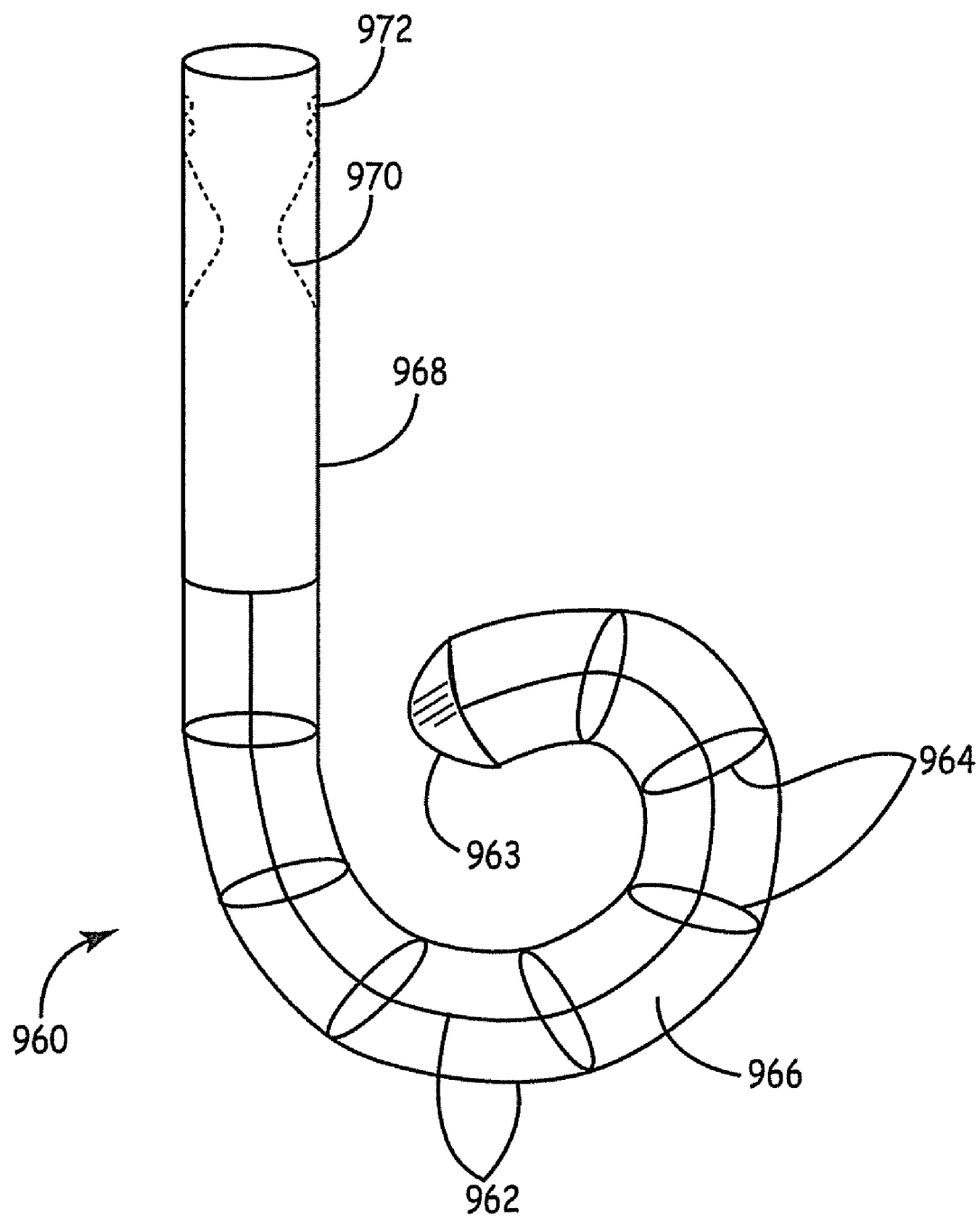
FIG. 9E depicts an alternative embodiment of a catheter with a cage and a seat.

FIG. 9E depicts another alternative catheter 960 with a plurality of longitudinal structural members 962 secured at end piece 963 and structural rings 964 secured to members 962. Interior space 966 is caged by members 962, 964 and otherwise open to communicate with its surroundings. Tube 968 has flange 970 and internal ribs 972. The flange 970 may be used to seat a fluid collector (e.g., as adapted from FIG. 7) and ribs 972 may be used as fasteners to secure a securing device (not shown) for the fluid collector (not shown). Catheter 960 may be a component in a system that includes a reservoir or used directly inside the body, e.g., in the peritoneal space, and may be further provided with peritoneal and/or subcutaneous cuffs (not shown). The structural members may be coiled and joined by ring-shaped cross members to provide a framework. A semipermeable membrane that communicates with a reservoir external to the patient can be reversibly removed/placed in the catheter or the membrane can be a permanent part of the catheter.

The structural members may be rigid or flexible and may be made of suitable biocompatible materials, e.g., stainless steel, polyurethane, polytetrafluoroethylene, or PEEK. The structural members may be joined to an endpiece rounded for ease of insertion and indwelling. In some embodiments, the semipermeable membrane is attached to a connector, e.g., the connector has threads to connect to the portion of the catheter that remains outside the body. The membrane can be filled and pushed into the catheter, or pushed through the catheter with a blunt tool, e.g., a plastic rounded rod. In some embodiments, the structural members are part of a unit integral to the membrane which is joined to the endpiece; a single unit can thus be eased in and out of a catheter.

In certain embodiments, an outer catheter and an inner catheter are used. The outer catheter is placed in the patient as an indwelling catheter. The inner catheter is advanced through the outer catheter and deploys a semipermeable membrane in communication with one or more lumens of the inner catheter, with one or more of those lumens being in fluid communication with a reservoir. The semipermeable membrane is exposed to the fluids of the body space where it is deployed and draws fluid into the reservoir by osmosis since the membrane contains solutes trapped inside the membrane.

The inner catheter may be completely contained within the outer catheter, or may extend past the distal end of the outer catheter.

Figure 9F:
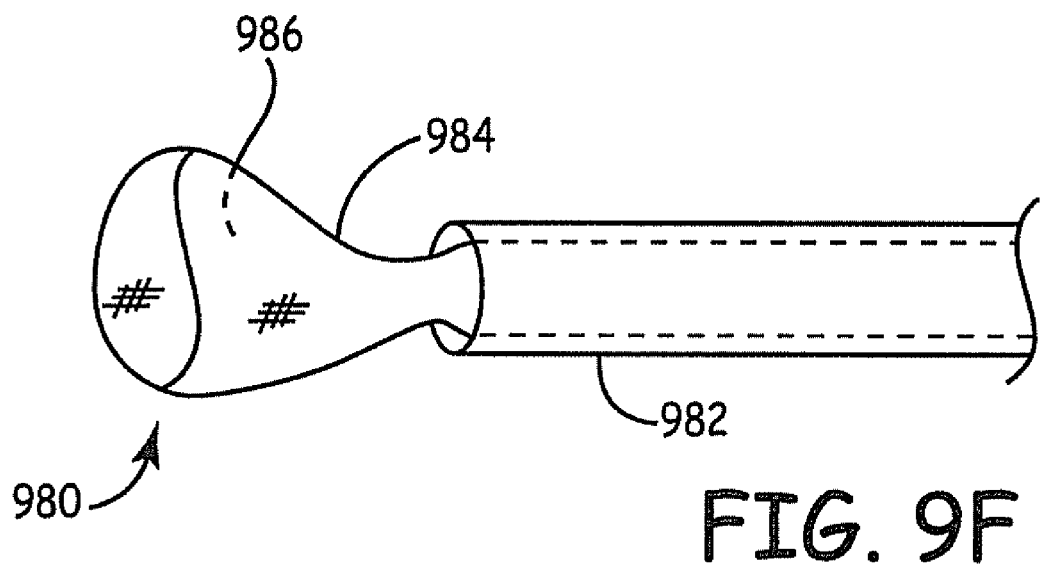
FIG. 9F depicts an outer catheter and an inner catheter that comprises a semipermeable membrane outside the outer catheter.
Figure 9G:
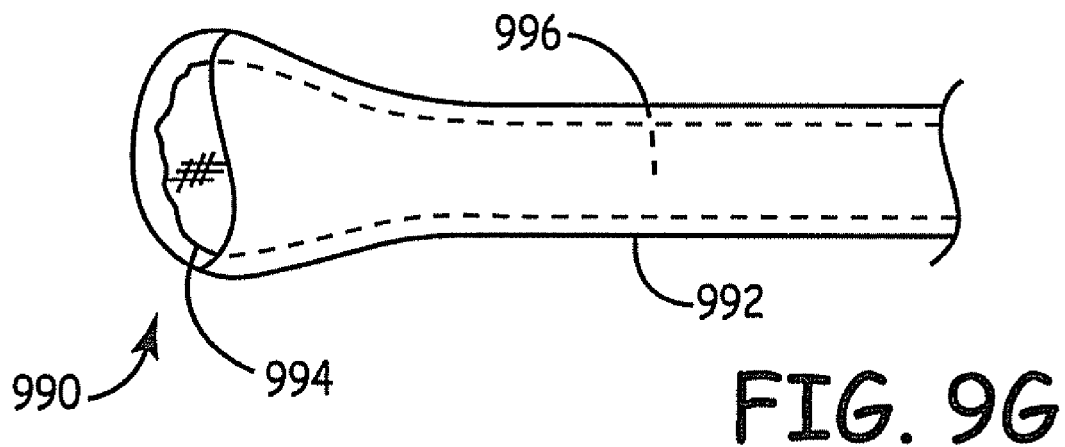
FIG. 9G depicts the embodiment of FIG. 9F with the membrane deployed inside the outer catheter.

FIG. 9F depicts system 980 with indwelling catheter 982 partially containing semipermeable membrane 984 that has lumen 986. FIG. 9G depicts system 990 with indwelling catheter 992 partially containing semipermeable membrane 994 that has lumen 996.

Figure 10A:
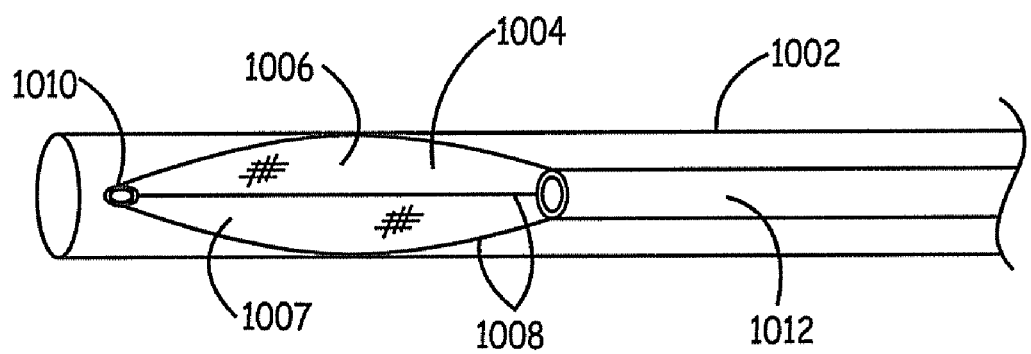
FIG. 10A depicts a fluid collection device internal to an outer catheter.
Figure 10B:
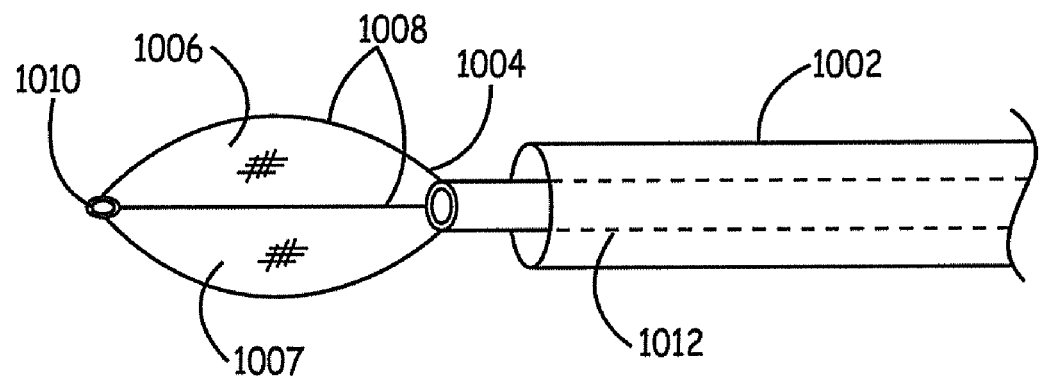
FIG. 10B depicts the fluid collection device of FIG. 10A in a deployed position external to the outer catheter.

For example, a fluid collecting device may be introduced through an outer catheter, with a semipermeable membrane portion being self-expanding by virtue of entry of fluids into the device, or with the membrane having integral self-expanding structural members. For example, FIG. 10A is a cross-sectional view of an outer catheter 1002 containing fluid collector 1004 that has semipermeable membrane 1006 with lumen 1007 and integral biased wire members 1008 joined to end piece 1010 and tubing 1012. FIG. 10B depicts fluid collector 1004 in an open, deployed position external to outer catheter 1002. The outer catheter 1002 may subsequently be withdrawn or left in place. Tubing 1012 is depicted with one lumen but may alternatively have a plurality of lumens, e.g., for simultaneous introduction and removal of lumen 1007 contents. Thus a self-deploying semipermeable membrane may be delivered through an outer catheter. The outer catheter may be placed in the subject and left in place as an indwelling catheter. The inner catheter may be advanced through the outer catheter and open when it exits the end of the catheter. The structural members may be biased to spring open when not restrained by the outer catheter. A semipermeable membrane may surround, or be attached to, structural members such that its interior space communicates through an inner catheter to a reservoir. The inner catheter may have two lumens that communicate with the interior of the catheter so that one lumen may provide fluid to the membrane interior space and the other lumen may withdraw the fluid.

Figure 11:
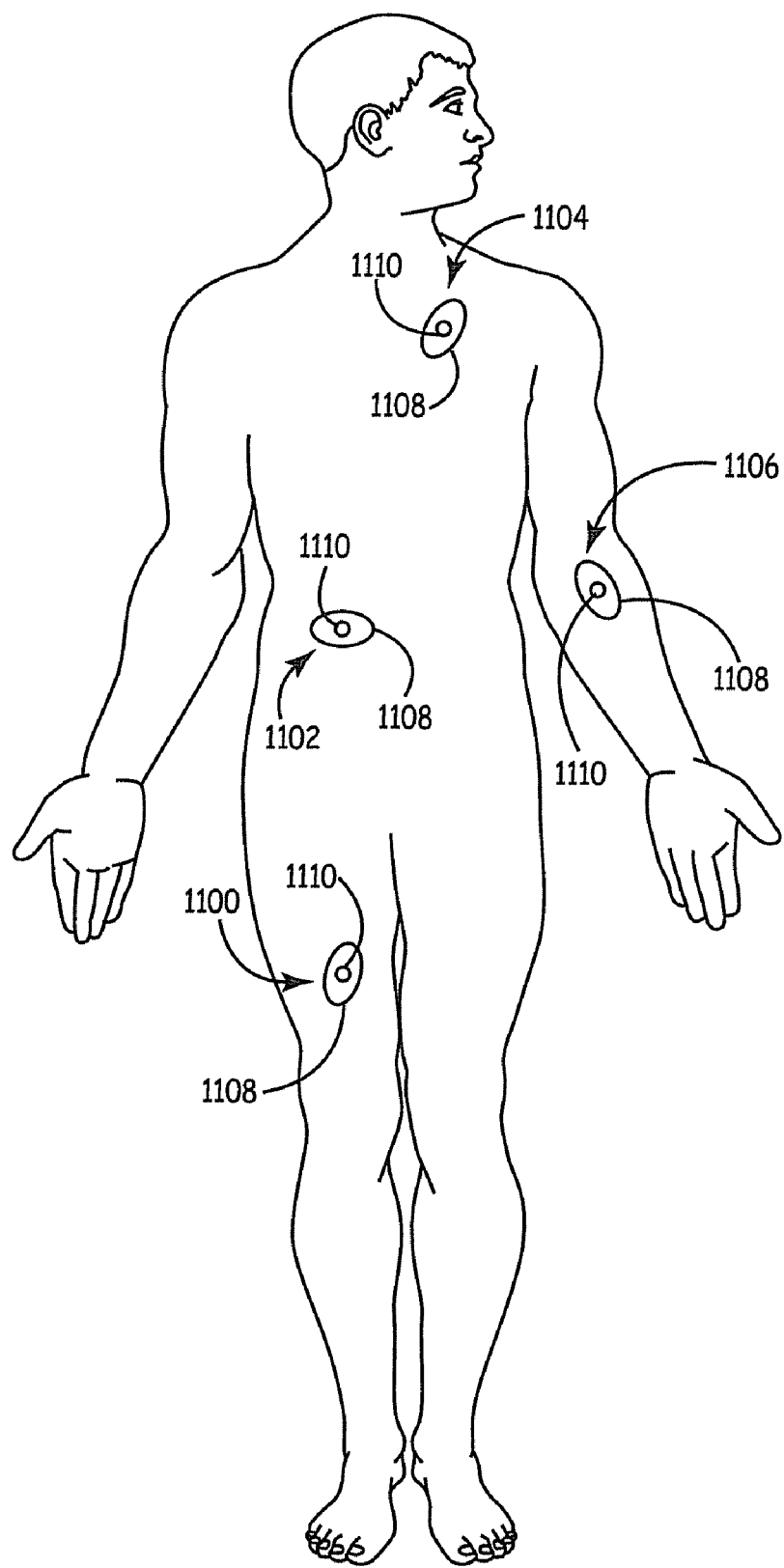
FIG. 11 depicts some applications of a fluid collection device.

FIG. 11 depicts examples of placement of a fluid collector. Placement may include, for example, lower limb 1100, abdominal trunk 1102, upper thoracic 1104, or upper limb 1106. Fluid collector 1108 comprises a lumen at least partially bounded by a semipermeable membrane in contact with a tissue for trapping osmotic solutes to create osmotic pressure to draw a fluid into the collector. The collector has a port 1110. As is evident, the various embodiments of collectors and features described herein may be combined to make a fluid collector. These positions indicate examples of where such collectors may be placed.

Figure 12:
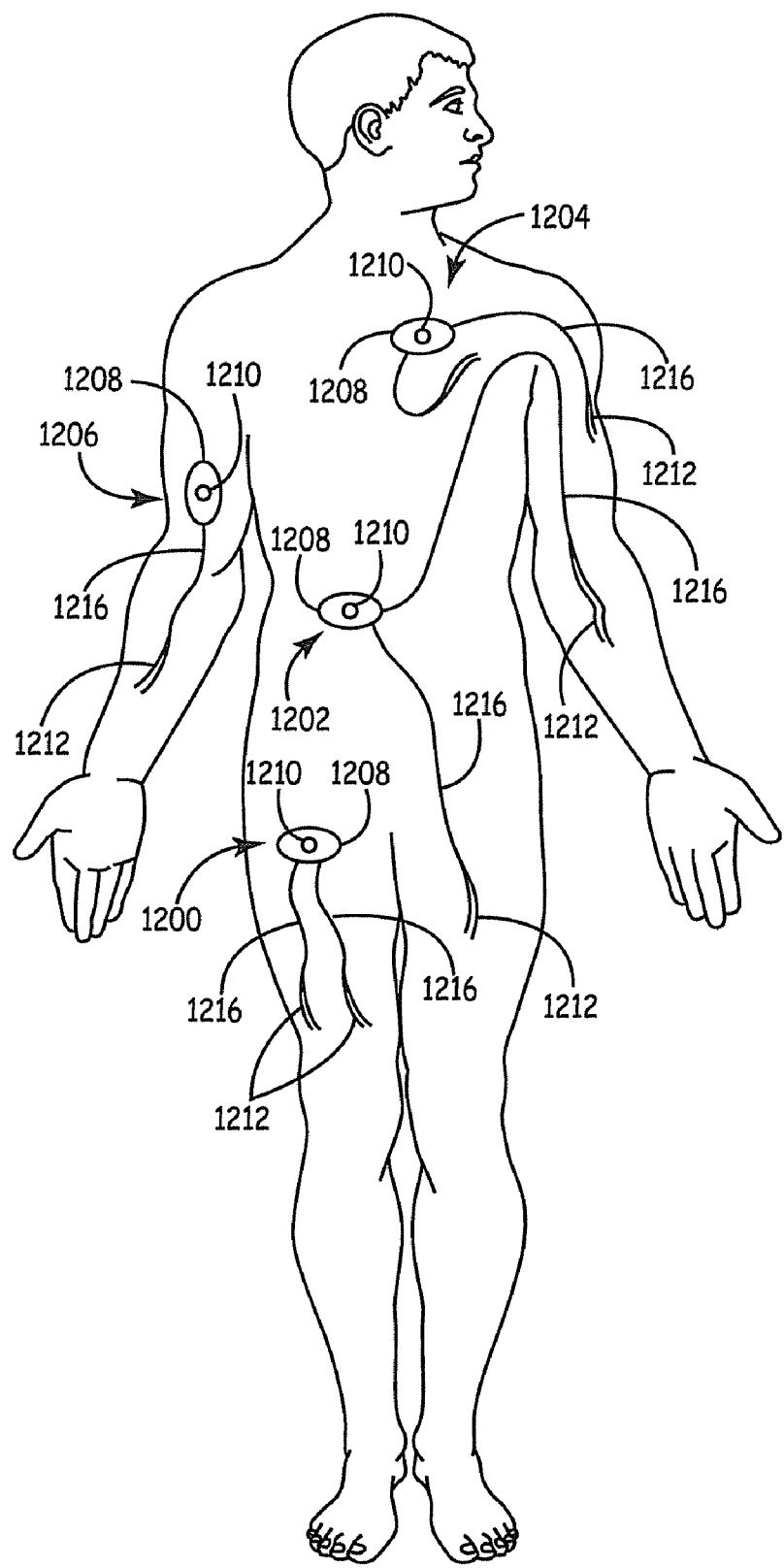
FIG. 12 depicts some applications of a fluid collection device that comprises at least one appendage to draw fluid into the device.

FIG. 12 depicts further examples of placement of a fluid collector. Placement may include, for example, lower limb 1200, abdominal trunk 1202, upper thoracic 1204, or upper limb 1206. Fluid collector 1208 comprises a lumen at least partially bounded by a semipermeable membrane in contact with a tissue for trapping osmotic solutes to create osmotic pressure to draw a fluid into the collector; in this embodiment, the semipermeable membrane 1212 is located distal to the reservoir 1214 of collector 1208, as indicated by the thickened portions of catheter(s) 1216. The collector has a port 1210. The semipermeable portions 1216 provide for points of entry of native fluids into the collector, which may be removed through reservoir 1214. The fluid collector may be internally placed or externally placed with at least a portion disposed interior to a patient. As is evident, the various embodiments of collectors and features described herein may be combined to make a fluid collector. These positions indicate examples of where such collectors may be placed.

Figure 13:
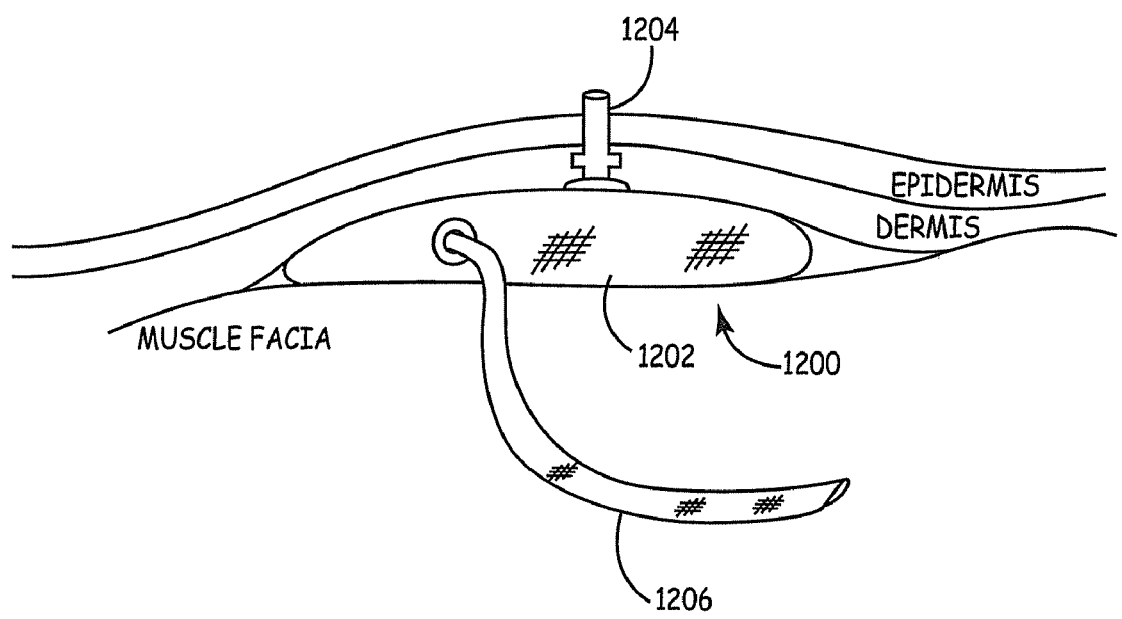
FIG. 13 depicts an example of placement of an internal reservoir.

FIG. 13 depicts an example of a subdermal reservoir placement. Fluid collector 1200 has reservoir 1202, port 1204, and catheter 1206. The reservoir and/or the catheter comprise a semipermeable membrane that at least partially borders a lumen that communicated with interior of reservoir 1202. As is evident from this disclosure, alternative embodiments have the semipermeable membrane at all or various locations of the reservoir and/or on the catheter, or have no catheter, have a port that is entirely implanted, or have no port but instead have a catheter to redirect fluid to other parts of the body.

Accordingly, fluid collector placement may be made to collect fluid from a lower limb, a lower trunk, an upper trunk, an upper limb, or other portions of the body. Some embodiments are directed to recovery of excess fluid in the pleural or lung area, with a collector, typically a catheter, being placed at or near the lung. Some embodiments are directed to placement of a fluid collector reservoir in a position that mimics a breast implant to provide a convenient and possibly cosmetically appealing option.

Implants of fluid collectors or fluid collector portions may be placed as needed for the intended application. Placement options include subglandular, subfascial, and submuscular, or mixtures of the same, e.g., subpectoral. A subglandular implant can be made, for example, between tissue and muscle, e.g., between breast tissue and the pectoralis muscle. This position resembles the plane of breast tissue and can also be cosmetically appealing to some patients in the case of a reservoir implanted at this location. An example of a subfascial placement is underneath a muscle fascia. For instance, underneath the fascia of the pectoralis muscle. An example of submuscular placement is below a muscle, for instance, below the pectoralis without release of the interior origin of the muscle. Subpectoral implantation may involve placement under the pectoralis major muscle to be partially under the pectoralis and the subglandular plane.

Figure 14:
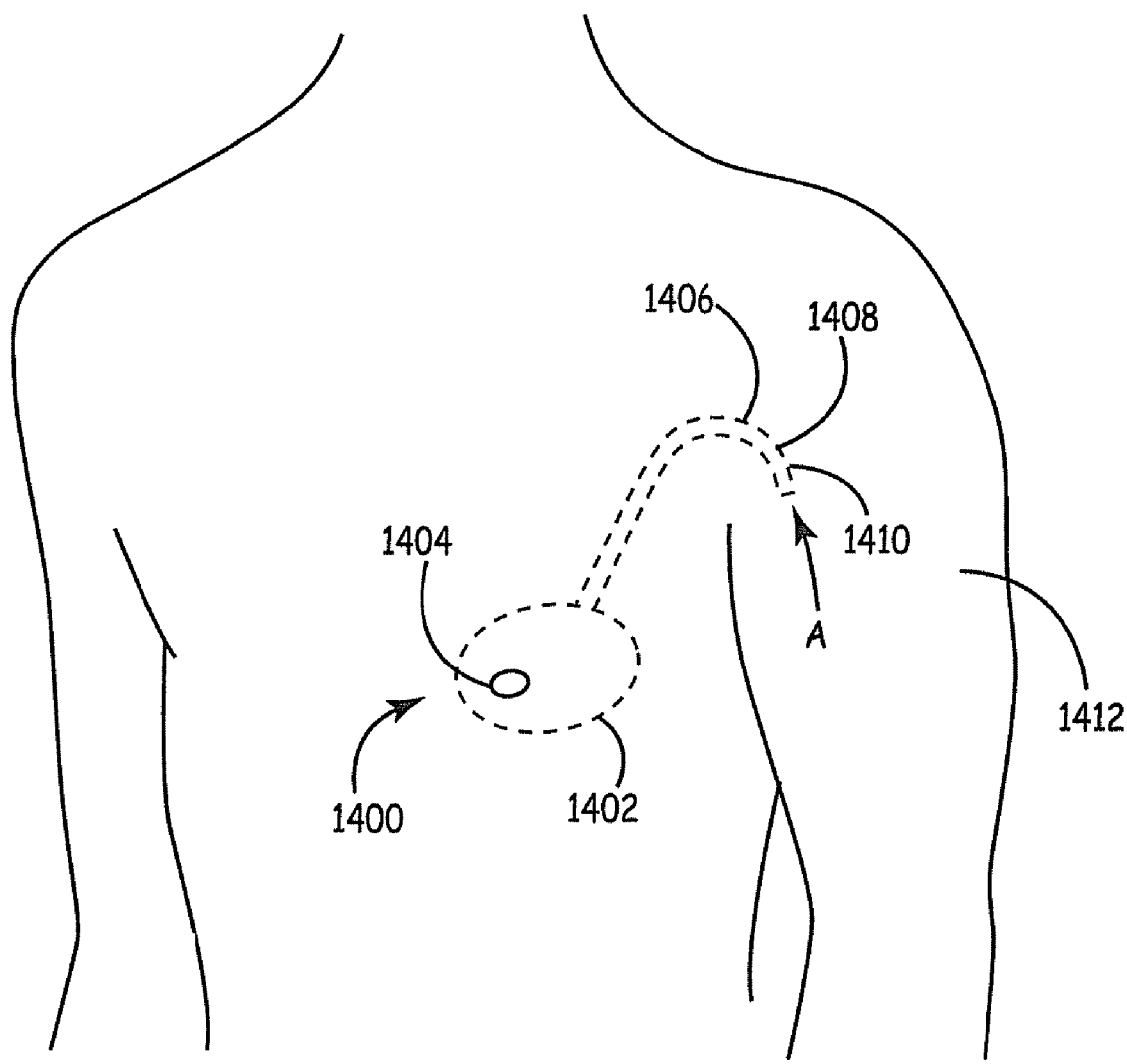
FIG. 14 depicts an example of placement of an internal reservoir and a collection appendage in the context of upper limb edema.

Fluid diffuses through the interstitial tissue of the patient so that withdrawals that are not fully in contact with the edemic tissue may nonetheless draw out fluids to create a movement of fluids out of the edemic tissue for relief of the edema. For instance, FIG. 14 depicts a subcutaneous placement with a transcutaneous port and a catheter extending to an edemic arm. Fluid collector 1400 has reservoir 1402 with transcutaneous port 1404 and catheter 1406. Catheter 1406 has distal region 1408 that comprises a semipermeable membrane 1410. Trapped osmotic solutes internal to the fluid collector create osmotic pressure to draw native fluids, indicated at arrow A, from edemic limb 1412. A user withdraws fluids from time to time from reservoir 1402 through port 1404. The catheter may extend fully into a edemic portion of a limb, be placed within a few inches of the edemic portion, e.g., 1 to 12 inches, or at a distance from the limb, e.g., 12 or more inches. As such, catheter 1406 in FIG. 14 may be omitted, with reservoir 1402 comprising at least one portion that has a semipermeable membrane to draw native fluids into the reservoir for collection.

Figure 15A:
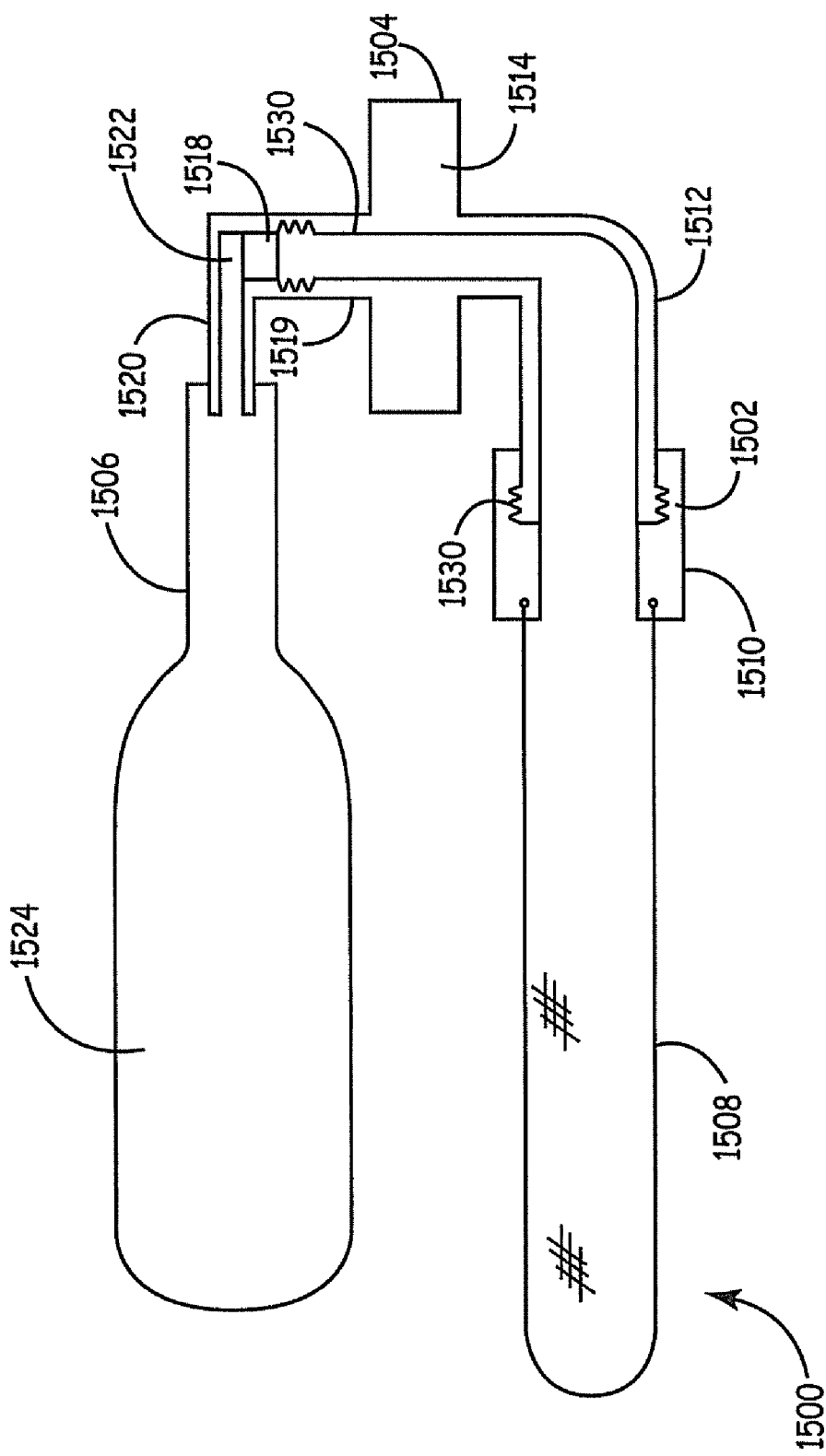
FIG. 15A depicts a fluid collection device.
Figure 15B:
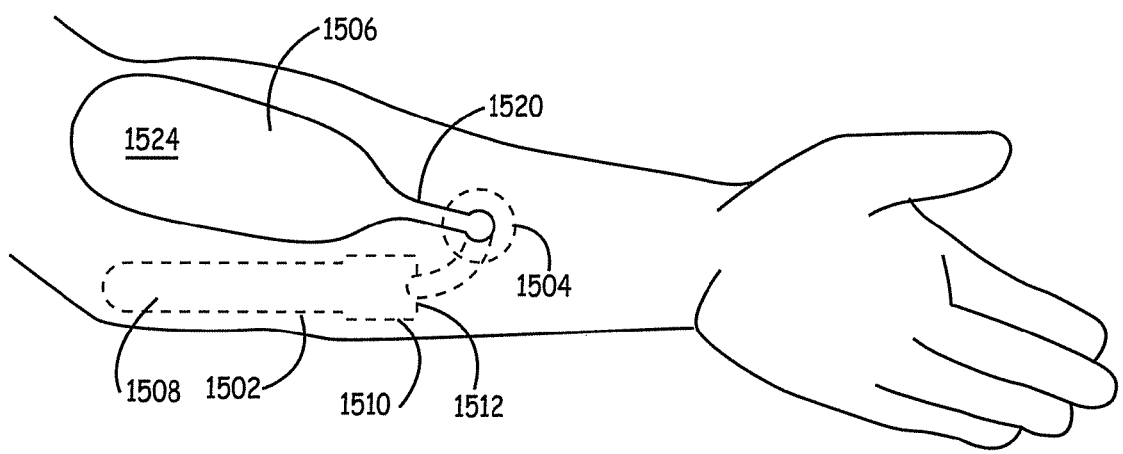
FIG. 15B depicts a placement of the device of FIG. 15A.

Another embodiment of a fluid removal device is depicted in FIG. 15. Fluid removal device 1500 has internal member 1502 for gathering physiological fluids, transcutaneous member 1504 for access to the internal member, and extracorporeal member 1506 to provide osmotic solutes. Internal member 1502 has semipermeable membrane 1508 (e.g., a hollow tube fiber or sintered construction) and connector collar 1510 that connects semipermeable membrane 1508 to the transcutaneous member. Transcutaneous member 1504 is a fluid port with connector 1512 to join to the internal member, skirt 1514 for subdermal placement, e.g., a suturing collar or porous anchor for ingrowing tissues, internal conduit 1516 that receives optional semipermeable membrane 1518, with external portion 1519 remaining outside the body. Extracorporeal member 406 has connector 1520 with bore 1522 communicating with reservoir 1524. In use, internal member 1502 is implanted internally, e.g., by a trochar, minimally invasive surgery, or incision with transcutaneous member 1504 being places under the skin of the patient with the external portion 1519 outside the body. Semipermeable membrane 1518 may be present. Extracorporeal member 1506 is filled with osmotic solute and connected to external fluid port portion 1519 via connector 1520. Osmotic solute in 1524 communicates with interior of semipermeable member 1518, which may be implanted filled with an aqueous medium in the absence of air so that it is internally wetted. When osmotic solute is present at a concentration that creates an osmotic pressure, physiological fluid flows into the device and diffuses through the device, including reservoir 1524. When reservoir 1524 is full or at a predetermined time, it may be replaced by a fresh reservoir, e.g., daily, twice daily, every other day, or once a week. Reservoir 1524 may be sized as needed for the application, e.g., from 100 ml to 10 liters; artisans will immediately appreciate that all ranges and values between the explicitly stated values are contemplated, e.g., 500 ml to 1500 ml at capacity. Semipermeable membrane 1518 may be used to enhance safety, bearing in mind that bacteria are generally too large to pass through membranes sized for osmotic applications; membrane 1518 may have a MWCO lower than the MW of trapped osmotic solutes in reservoir 1524. Device 1500 is depicted with a single semipermeable membrane 1508 but a plurality of such membranes may be used to enhance surface area and distribution with the patient 1550; e.g., by joining them to each other is a series or connecting them to internal member 1512 after adapting it with a plurality of connectors or other unions. Various fasteners 1530 may be employed for reversible or alternatively permanent union of the pieces.

As is evident, a catheter comprising a semipermeable portion may be implanted internally in a patient at a desired location in combination with a transcutaneous port that provides for reversibly connection to a reservoir that fluidly communicates with a lumen of the catheter, with the system containing trapped osmotic solutes that creates an osmotic pressure to draw fluid into the lumen and the reservoir; the reservoir may be periodically removed, re-loaded and re-used, or disposed of with a fresh unit being used in its place. Alternatively, a larger reservoir may be used. The osmotic solutes of the catheter may be introduced or withdrawn through the port. The semipermeable membrane may be removable and replaceable through the port.

Figure 16C:
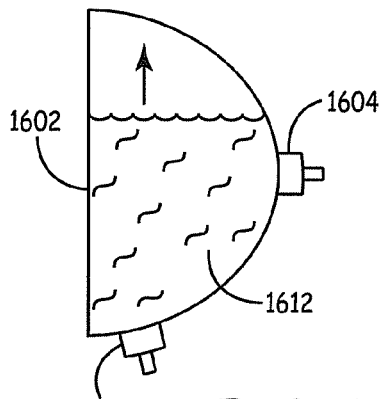
FIG. 16C depicts an alternative embodiment of a fluid collection device.
Figure 16A:
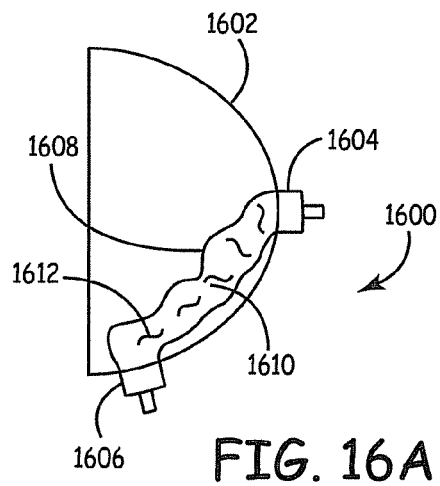
FIG. 16A depicts a fluid collection device.
Figure 16B:
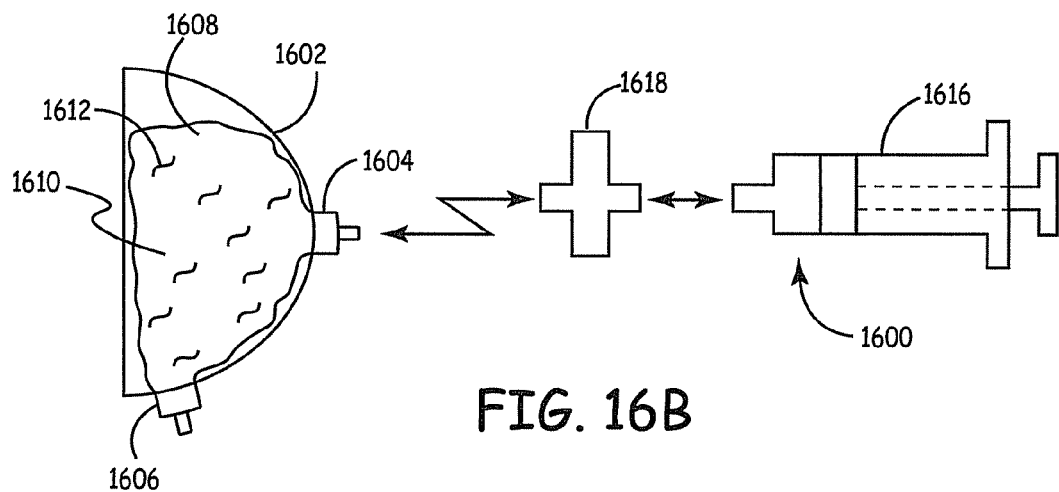
FIG. 16B depicts the device of FIG. 16A after collection of fluid and in the context of a system that includes a fluid withdrawal device.

FIGS. 16A and 16B show a system 1600 with a housing 1602 partially (FIG. 16A) or more fully (FIG. 16B) filled. Housing 1602 has port 1604 that may be transcutaneous (meaning having a portion that passes out of the body through the skin) or percutaneous (meaning the port has no portion external to the body but accessible through the skin), and a fluid egress 1606 that provides for fluid to be collected, e.g., with a catheter with a semipermeable portion connected thereto and placed internally to a patient. The term egress refers to an exit point. A point of exit for a fluid may often serve as a point of entry, but such is not always the case, as in a one-way-valve-egress or in certain methods that use an opening to introduce a fluid but not withdraw it. A semipermeable membrane 1608 serves as the reservoir and provides lumen 1610 that is loaded with osmotic solutes 1612 and is fluidly connected to port 1604 and egress 1606. As fluid is drawn into lumen 1610, it expands the membrane. Syringe 1616 with optional syringe filter 1618 may be used to move fluids in and out of the lumen. The syringe filter may be used to provide an extra degree of sterility, e.g., with a filter sized to screen-out bacteria, and/or sized to retain osmotic solutes 1610 in the lumen, e.g., with the filter being too fine to allow the trapped solutes to be removed. These figures show an expandable/collapsible semipermeable membrane inside a housing, which may be altogether rigid, altogether flexible and/or collapsible, or partially one or the other. Alternatively, as at FIG. 16C, the housing 1602 can have no semipermeable membrane component and/or can have no membrane and simply communicate with the contents of the semipermeable membrane interior to the patient. A syringe (as depicted) or syringe pump, peristaltic pump, or gravity feed/drainage may be used to fill or empty the reservoir.

Figure 17:
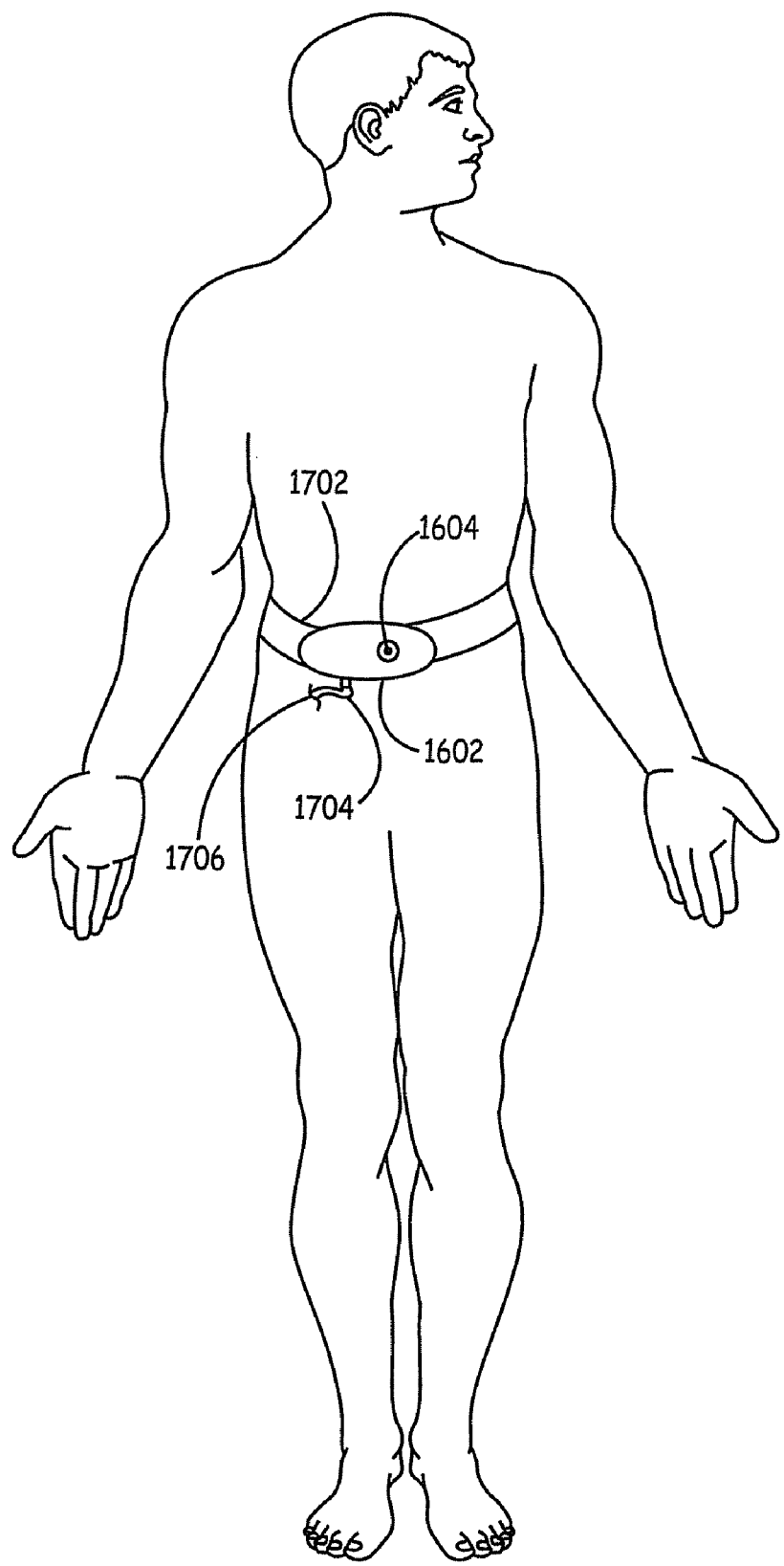
FIG. 17 depicts a fluid collection system in use on a patient.

Alternatively, the devices of FIG. 16 may be adapted for use with reservoir 1602 external to the patient. As at FIG. 17, the reservoir 1602 may be secured to the patient with belt 1702 and a catheter 1704 affixed to egress 1606. Catheter passes transcutaneously into the patient at 1706 and is in fluid communication with a lumen at least partially bounded by a semipermeable membrane. Reservoir 1602 and catheter 1704 are loaded with osmotic solutes to draw fluids in.

Figure 18A:
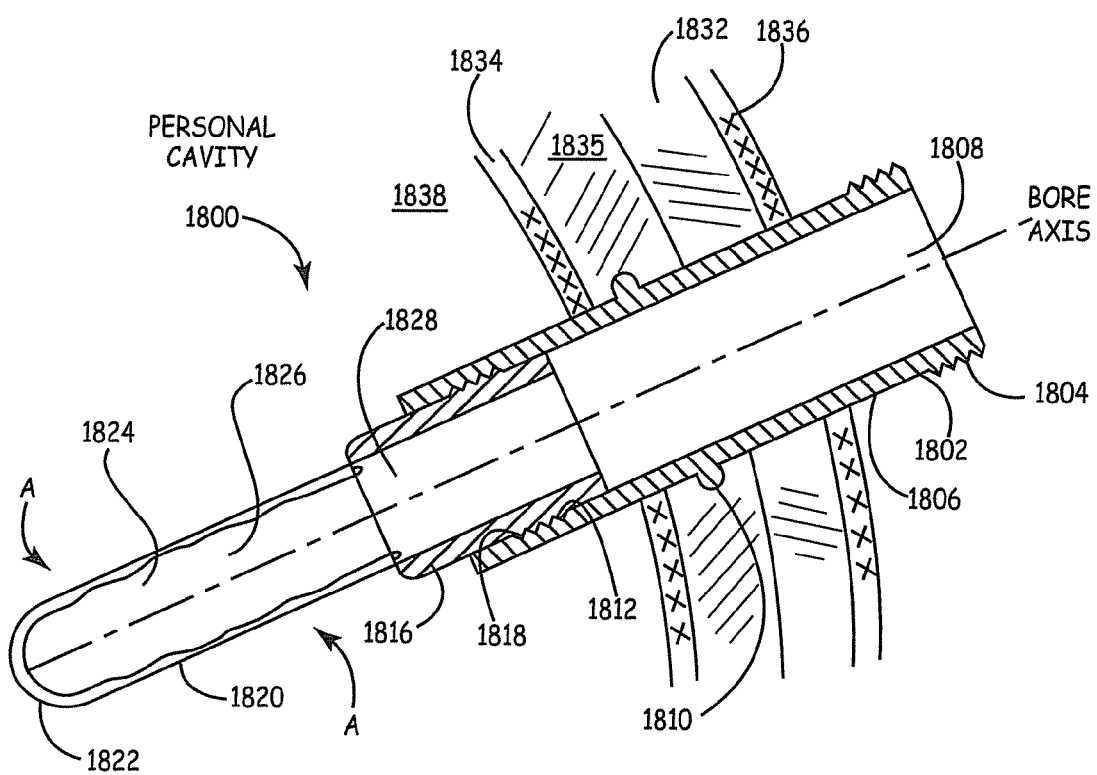
FIG. 18A is a cross-sectional view of an access that provides for pass-through and seating of a fluid collection device.
Figure 18B:
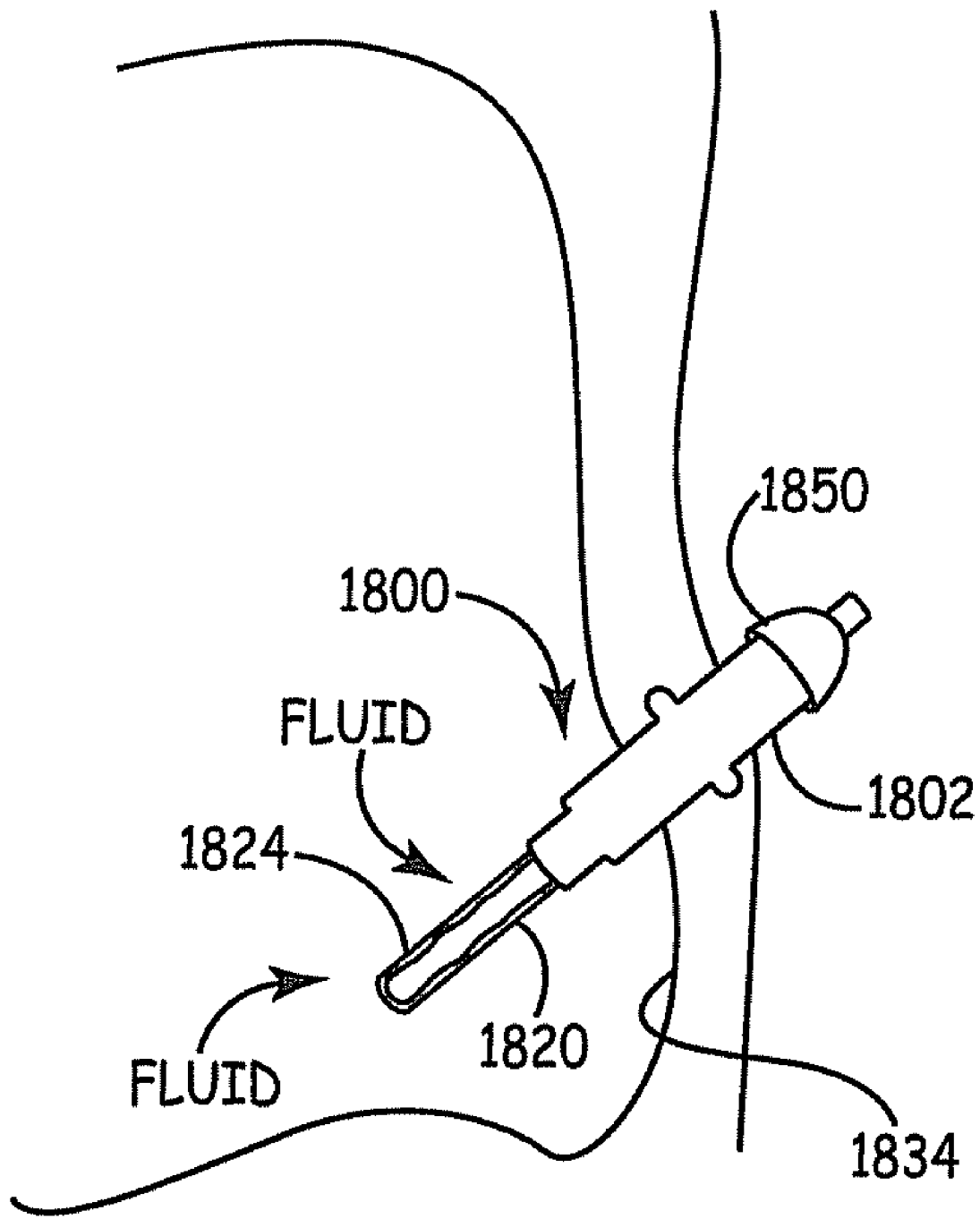
FIG. 18B is a cross-sectional view of the device of FIG. 18A in place in a peritoneal space.

FIG. 18A depicts an example of some of the various features already described in combination with each other as placed in a peritoneal cavity for collection of fluid therefrom by osmotic flow. System 1800 has transcutaneous port 1802 has external threads 1804 on cylinder 1806, bore 1808, cuffs 1810, and internal threads 1812. Semipermeable membrane assembly 1814 has collar 1816 with external threads 1818, structural members 1820 that join to collar 1816 and endpiece 1822, and semipermeable membrane 1824 that bounds lumen 1826 that is fluidly connected to bore 1828 of collar 1816. In use, port 1802 is surgically placed transcutaneously, e.g., as depicted with cuffs 1810 in adipose layer 1830, which lies between dermis 1832 and peritoneal membrane and fascia 1834. Epidermis 1836 is external to the dermis. Assembly 1824 is passed through bore 1808 and screwed into threads 1812 with assembly threads 1818. Alternative fastening systems may be employed and/or a flange to nest assembly 1824 and/or a securing fastener may be placed to further secure assembly 1824. Assembly bore 1828 is in fluid communication with bore 1808 and both are in fluid communication with lumen 1826. Lumen 1826 is loaded with trapped osmotic solutes and fluid, as at arrow A, is drawn in from peritoneal space 1828. A cap (not shown) may be used to cover port 1802, e.g., by screwing onto threads 1804. Port 1802 may be secured to tubing that leads to a reservoir or other fluid collection or disposal system. FIG. 18B depicts an exemplary use in a peritoneal cavity, with system 1800 transcutaneously placed and loaded with osmotic solutes to draw fluid into the collector. Connector 1850 is depicted for connection to other components as desired (not shown). As applied to peritoneal placement, system 1800 is loaded with osmotically trapped solutes to create an osmotic pressure to drive fluids into the device through the semipermeable membrane.

As is evident, removal of fluids by use of devices having trapped osmotic solutes can be used to remove unwanted materials from the patient that are in the patient's fluids, as in hemodialysis or peritoneal dialysis. The fluids collected into the osmolar-collection devices may be removed continuously or from time to time. One benefit of this approach is that users may consume liquids and the osmotic pressure and flow into the system can be adjusted to remove fluids at a desired rate. Osmotic pressure may be adjusted by increasing or decreasing the amount of trapped osmotic solutes. The surface area of the semipermeable membrane can be sized to increase or decrease a flow rate.

Accordingly, a method of cleansing fluids generally in a patient is to adjust fluid intake and fluid removal. The fluid may be collected from the peritoneal space or other tissues.

For instance, a patient may be directed to consume certain amounts of fluids, e.g., water, water with osmotic solutes, osmotically balanced drinks, beverages. Or the patient may be directed to drink a volume of liquid proportionate to, or matched to, the fluid volume that is collected. Or a user or patient may alternatively or additionally adjust the removal of fluids from the patient as desired, e.g., by more frequent replacement of the osmotically loaded solutes in the system or more frequent redirection of fluids out of the collector. In some embodiments, a user is directed to drink between about 0.5 and about 5 liters of a fluid daily; artisans will immediately appreciate that all ranges and values between the explicitly stated values are contemplated, e.g., 1-3 liters or 0.5-2 liters. In some embodiments, between about 0.5 to about 5 liters are daily removed, with adjustments being made as needed to provide for a desired volume of fluids in the patient.

Figure 19:
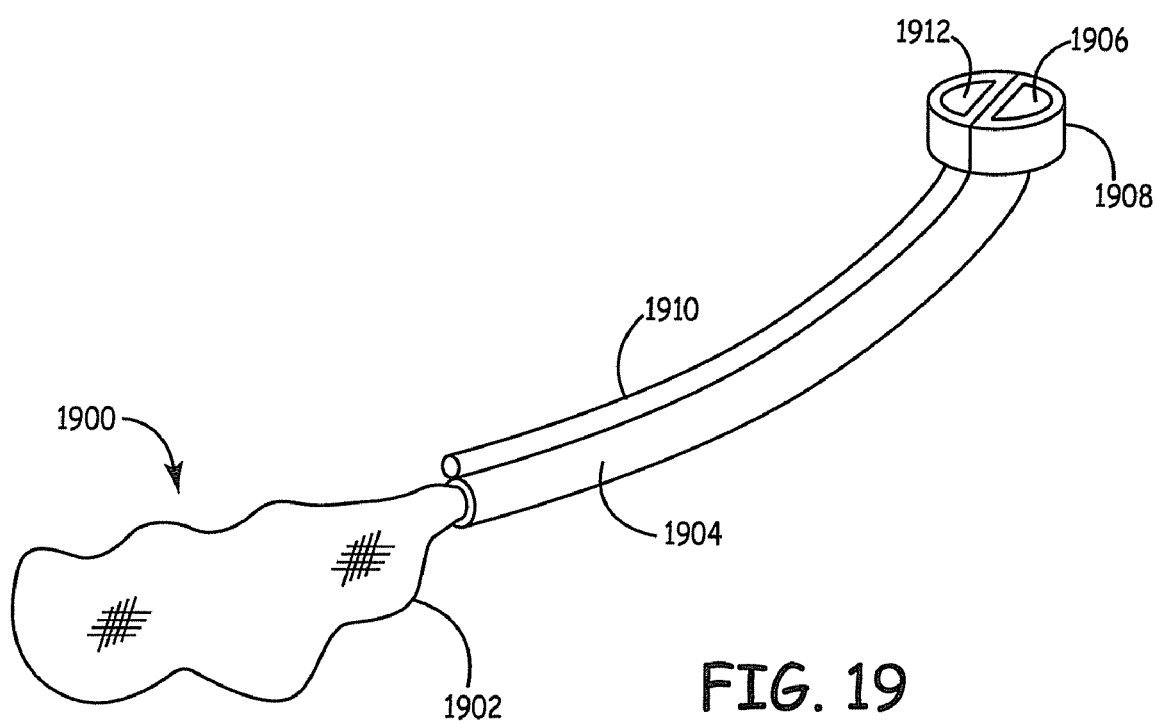
FIG. 19 depicts a fluid collection device with a lumen for introducing material directly into a patient.

FIG. 19 depicts an alternative system 1900 with semipermeable membrane 1902 defining a lumen in fluid communication with lumen of catheter 1904 that is connected to bore 1906 of port 1908. A second lumen or catheter 1910 is also connected to port 1908 via separate bore 1912. An example of use is the placement of system 1900 in a patient with membrane 1902 internal to the patient to collect fluids internal to the patient, e.g., in a peritoneal space or other tissue. Fluids may be introduced via catheter 1910 into the patient. In the context of placement in peritoneal tissue, catheter 1910 may be used to introduce or remove fluid. In some embodiments, substantially conventional peritoneal dialysis is conducted with osmotically-driven fluid collection serving as an adjunct system to remove fluids. Accordingly, in some embodiments, a conventional peritoneal dialysis solution is introduced into the peritoneal space and fluid is withdrawn from that space by an osmotic process. Thus catheter 1910 may be used to introduce or remove fluids from time to time, e.g., to introduce dialysate for dialysis or to expand the peritoneal space. In other embodiments, the peritoneal space is expanded by injection of fluids prior to introduction of a fluid collection device.

It is possible to create large driving forces to collect fluids; one benefit is that the driving force may be adjusted as desired to achieve a desired fluid collection rate. Similarly, the membrane of the fluid collection device may be changed out through an access port so that further control over the MWCO of collected materials may be exercised. These features can be manipulated to extend the useful life of a peritoneal dialysis programme when the peritoneal membrane begins to fail or the peritoneal dialysis process otherwise begins to fail due to changes in the patient's physiological state.

In other embodiments, a catheter with a plurality of lumens communicates with a lumen of a fluid collection device, with the catheter lumens being available for simultaneous introduction and withdrawal of fluid.

Methods include withdrawing fluid from a patient suffering from congestive heart failure (CHF). In the case of CHF, lung edema is part of the vicious cycle of CHF progression such that removal of excess fluid is useful.

In some embodiments, an appendage for osmotically-driven fluid collection (e.g., hollow tube fiber, catheter or a plurality of catheters) is threaded or tunneled into a region at or near a lymph collection node, e.g., within about 1, about 2, about 3, about 4, or about 5 cm. As already described, a catheter may be introduced into the patient and a fluid collection device introduced through the catheter, which may be fully or partially withdrawn, or left in place. It may be useful to place the collectors near the highest mediastinal node (position 1) or other nodes, e.g., (i) Superior Mediastinal Nodes 1-4: 1. Highest Mediastinal: above the left brachiocephalic vein; 2. Upper Paratracheal: above the aortic arch, but below the left brachiocephalic vein; 3. Pre-vascular or Pre-vertebral—these nodes are not adjacent to the trachea like the nodes in station 2 since they are either anterior to the vessels or behind the esophagus, which is prevertebral; 4. Lower Paratracheal (including Azygos Nodes): below upper margin of aortic arch down to level of main bronchus, (ii) Aortic Nodes 5-6: 5. Subaortic (A-P window)-nodes lateral to ligamentum arteriosum, these nodes are not located between the aorta and the pulmonary trunk, but lateral to these vessels; 6. Para-aortic (ascending aorta or phrenic)-nodes lying anterior and lateral to the ascending aorta and the aortic arch. (iii) Inferior Mediastinal Nodes 7-9: 7. Subcarina; 8. Paraesophageal (below carina); 9. Pulmonary Ligament, nodes lying within the pulmonary ligaments (iv) Hilar, Interlobar, Lobar, Segmental and Subsegmental Nodes 10-14: 10-14: these are located outside of the mediastinum.

Procedures for tunneling that may be adapted to this and other embodiments after reading this disclosure are described, e.g., U.S. Pat. Nos. 5,234,438, 5,782,841, 5,885, 217, 6,004,326, and 7,018,384. As already described, a catheter may, e.g., exit the body directly, be part of a system to redirect fluid, or interface with a reservoir inside or outside the patient. For instance, a reservoir may be implanted in a pocket analogous to a breast implant or a cardiac pacemaker, with an appendage placed at or near a lung site. The reservoir may have a transcutaneous or percutaneous port. Fluid may be withdrawn periodically or on demand.

Chronic wounds, e.g., pressure ulcers, decubitus ulcers, or skin lesions may be treated. In these methods, a fluid collection device is introduced internally to the patient, e.g., subcutaneously or subdermally, in or near (within about 1, about 2 about 3, about 4, or about 5 cm) the wound site. A semipermeable membrane with a lumen of trapped solutes, or other device described herein, draws fluids out of the wound area. The drainage of waste fluid and introduction of fresh interstitial fluids (oxygenated and nutritive) serves to promote healing. Drugs may be introduced at the same time across the membrane (e.g., VEGF, IGF-I, IGF-II, EGF, FGF, bFGF, antimicrobials, antifungals, antibiotics).

Ascites is marked by a build-up of fluid in the peritoneal space, and can also cause edema in other areas. Devices and methods described herein may be used to remove such fluid. In some embodiments, the MWCO of the semipermeable membrane is adjusted to exclude albumin, e.g., is 40,000 or less. In contrast, paracentesis, a method of removing fluid from the peritoneal space, often removes albumin and harms the patient. Shunts may also be used. Conventional shunts used are portacaval shunt, peritoneovenous shunt, and the transjugular intrahepatic portosystemic shunt (TIPS). These conventional shunts are essentially tubes.

Figure 20:
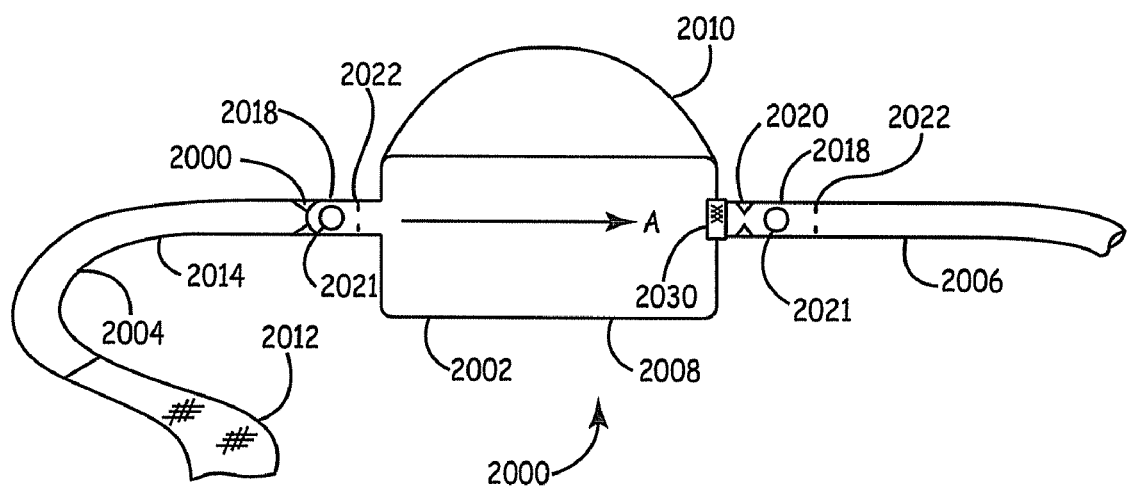
FIG. 20 is a cross-sectional view of a fluid collector for collecting fluid and redirecting the collected fluid.

An alternative shunting system, for ascites or other applications, uses a device as disclosed herein that includes a semipermeable membrane and a pumping mechanism. The device is loaded with trapped osmotic solutes to actively pull fluids in, and the pump serves to provide motive force to move the fluids out of the device to the intended site. The device may further comprise one or more check valves or other valves to provide unidirectional fluid movement. And, for instance, an adjustable flow control valve may be included. FIG. 20 is a schematic depiction of one such arrangement. System 2000 has manually operated pump 2002, fluid collector 2004, and catheter 2006. Pump 2002 has a housing 2008 that forms a container with a siding 2010 that is a flexible diaphragm. Fluid collector 2004 has a semipermeable membrane 2012 connected to catheter 2014 that connects to housing 2008. One-way valves 2018 have a ball seat 2020, ball 2021, stops 2022 for the ball, and provide for flow in a direction as indicated by arrow A. The semipermeable membrane 2012 is placed in a tissue area and, when the device is loaded with osmotic solutes, fluid flows into the device. A user presses diaphragm 2010 to force fluid in pump 2002 to move through filter 2030 and into catheter 2006, from whence it exits. One-way valves 2018 prevent undesired backflow. The depicted ball valve allows for the pump interior 2008 to be in fluid communication with the fluid collector 2004 until the pressure in the pump is increased and fluid is forced back into the collector, at which point the valve shuts. The filter 2030 may be sized to prevent release of trapped osmotic solutes. The pump may be manually-actuated or remotely or automatically operated.

A variety of embodiments for treating edema have already been described. For instance, a limb with poor or overloaded lymphatic drainage can directly receive a semipermeable membrane connected to a reservoir of osmotic fluid to directly remove excess native fluid. In the case of edema, patients have few options for fluid removal, and direct removal by osmotic pressure may avoid surgeries or provide an alternative to diuretic programs, which can be effectively used only until resistance is developed. In some cases, lymphatics are fully or partially blocked and drain the afflicted body portion slowly or not at all such that systemic diuretic treatment is never effective.

Figure 21:
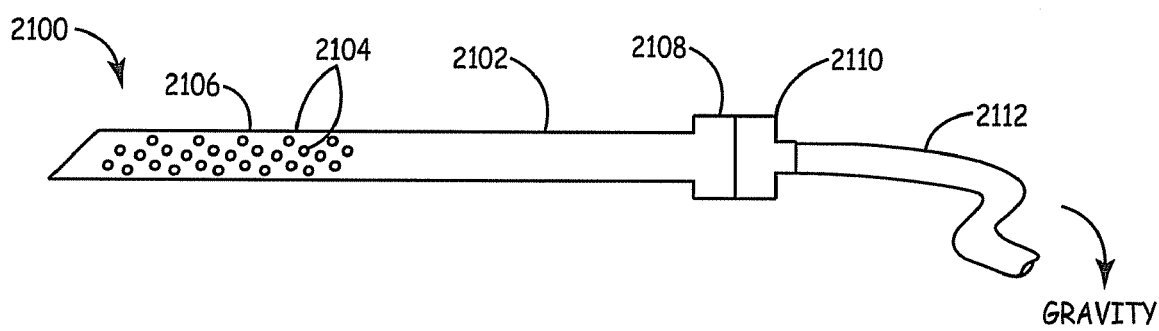
FIG. 21 depicts a prior art Southey tube.

One prior art approach to edema is use of the Southey tube (FIG. 21). Southey tube 2100 is a needle with perforations 2014 oat its distal end 2106 and a proximal end 2108 that is typically connected via a connector 2110 to a tube 2112 that empties into a reservoir outside the body that is filled by gravity, i.e., is located below the needle so that flow in the tube is down into the reservoir. The Southey tube tended to be part of a medical doctor's toolkit in the early 1900's but has since fallen into disfavor. In use, it was forced into the patient's edemic area and fluid in the area was allowed to drain as needed.

Figure 22A:
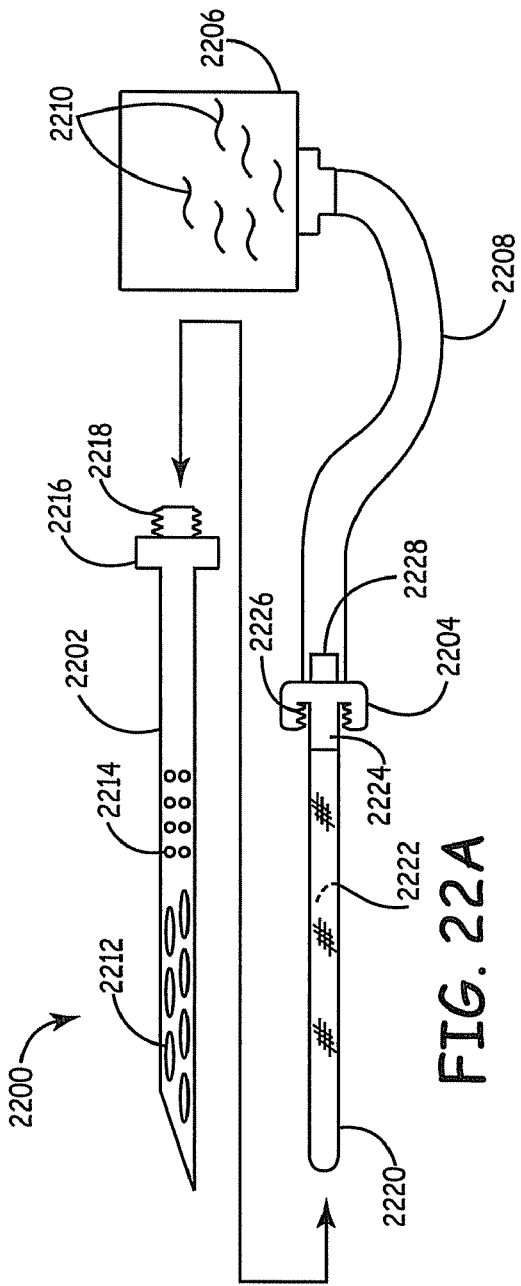
FIG. 22A depicts an embodiment of a fluid collection system.
Figure 22B:
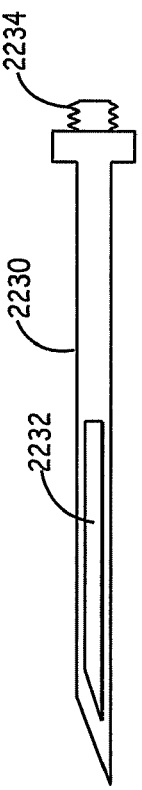
FIG. 22B depicts an alternative needle for the system of FIG. 22A.
Figure 22C:
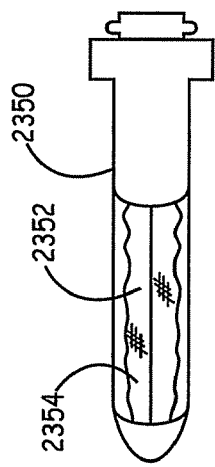
FIG. 22C depicts an alternative embodiment of a fluid collector for use in system of FIG. 22A.

A perforated or slotted needle may be used in combination with an insert that includes a semipermeable membrane that at least partially bounds a lumen for collecting fluids. Many suitable embodiments have already been described. In one method, the tube is placed in the patient and allowed to provide drainage and the insert is later introduced, e.g., when fluid flows slows or ceases, or for long-term drainage. FIG. 22A depicts an example. System 2200 has needle 2202, insert 2204, and reservoir 2206 with connecting tubing 2208. The system may be loaded with trapped osmotic solutes 2210. Needle 2202 has openings, e.g., slots 2212 or and/or round perforations 2214, and a connector 2216, here depicted with threads 2218 but other fasteners may be used. Insert 2204 has semipermeable membrane 2220 that partially bounds lumen 2222 that is joined to collar 2224 that has fastener 2226 to engage the needle connector and fastener 2228 for connection to tubing 2208. FIG. 22B is an alternative embodiment of a needle, with needle 2230 having a large opening 2232 and connector 2234. FIG. 22C is an alternative embodiment of a needle, with blunt needle 2350 having structural members 2352 that provide access to internal fluid collecting semipermeable membrane 2354.

Figure 23:
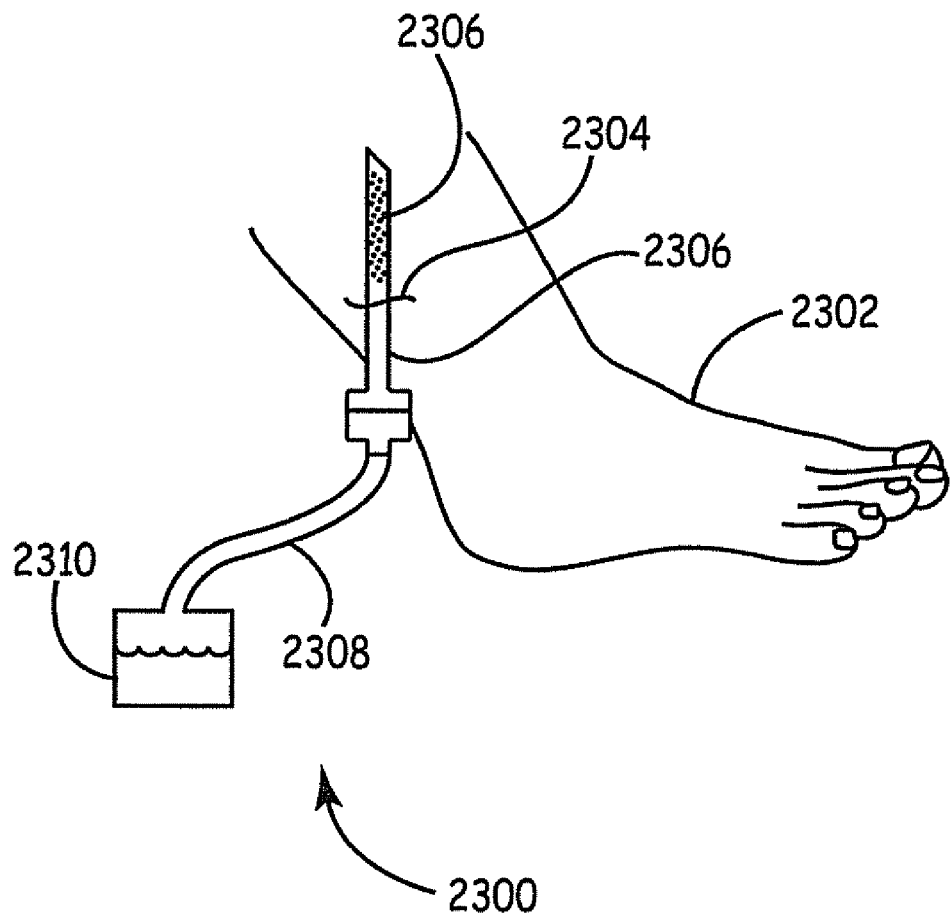
FIG. 23 depicts prior art use of prior art Southey tube.

FIG. 23 depicts a prior art Southey tube system 2300 in use. Edemic limb 2302 is transcutaneously pierced at entry point 2304 by Southey tube 2306. Tubing 2308 provides gravity drainage to waste collector 2310.

Figure 24:
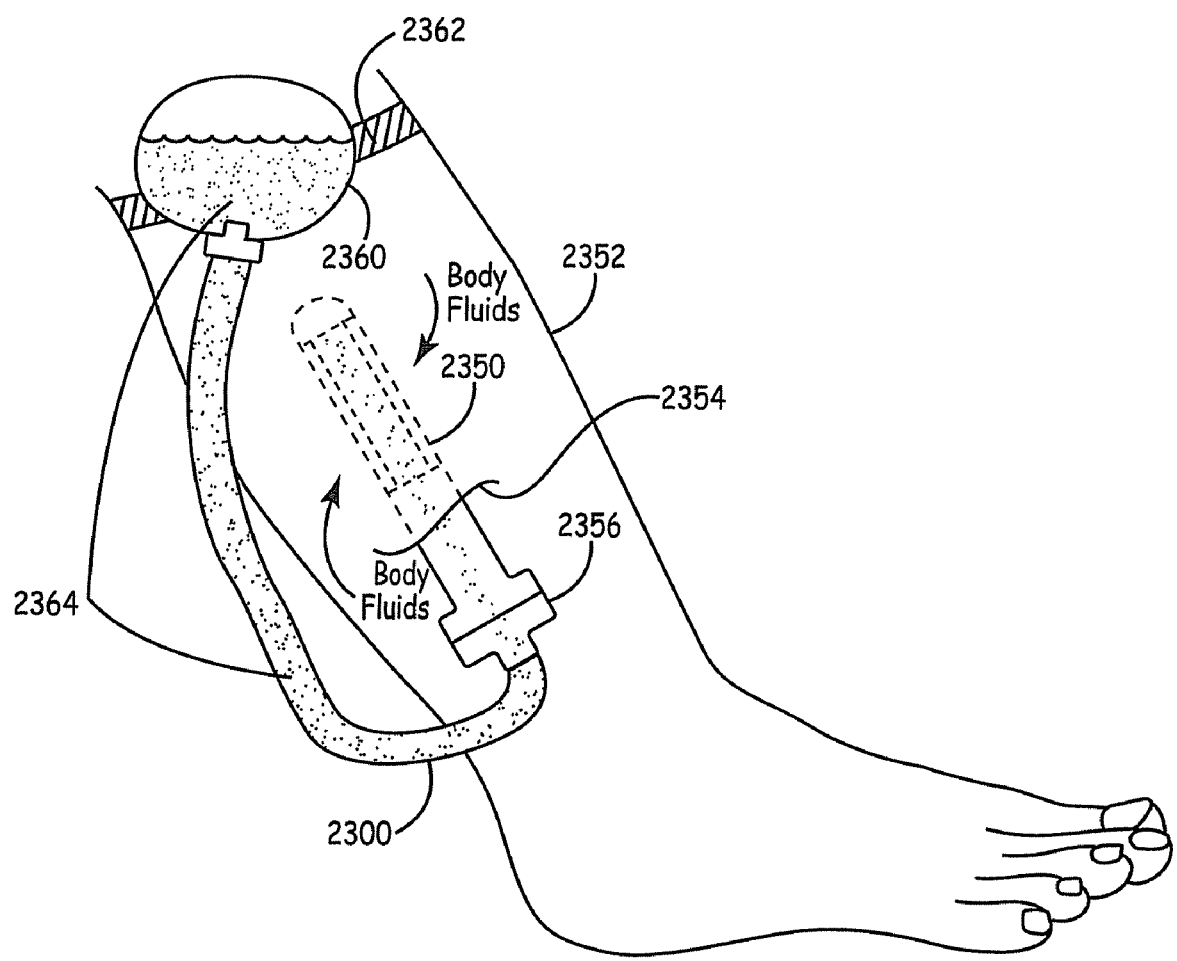
FIG. 24 depicts an application of the embodiment of FIG. 22C.

FIG. 24 depicts the embodiment of FIG. 22C in use. Blunt needle 2350 is in place in edemic limb 2352, and has been placed through transcutaneous entry point 2354 Connector 2356 is connected to tubing 2358, which is connected to container 2360, which is secured by strap 2362 to the patient. Trapped osmotic solutes 2364 provide osmotic force to draw native fluids into the device, as at arrows labeled "body fluids". The fluid from the patient can readily flow up, against gravity, into the container since the osmotic pressure can be set to overcome gravity. A benefit of this feature is that the patient may be ambulatory through the treatment. Another benefit is that osmotic pressure in the device will collect more fluid than can be collected with the Southey Tube method because the osmotic pressure draws fluid even after internal pressures in the patient are not favorable for expelling fluid without assistance. In some embodiments, a disposable insert is provided to the patient for placement into the needle or catheter. The patient disposes of the insert and replaces it as needed. An indwelling needle or catheter can also be provided with a cap or other closure for the user to fix to the same in between treatment sessions.

Another application is for catheters. Catheters are often used for drainage, either short-term after a surgery, or longer-term. The catheters are often connected to a waste collector or allowed to drain into bandages. Use of an osmotic fluid collection system can facilitate removal of fluids. Many embodiments have already been described for making a combination of a catheter with such a fluid collection device as will be evident to artisans reading this disclosure. In some embodiments, the catheter is equipped to reversibly receive an osmotically-driven fluid collector so that the catheter may be operated with or without such a collector. Another embodiment is a fluid collection device that can be passed through a catheter and into a patient to collect fluids without removal of the catheter. The pass-through device can be entirely within the catheter, within the catheter except for a portion that passes out of the catheter into the patient, and/or have a portion outside the patient, e.g., a tube or an external reservoir. Or the catheter can be provided with a fastener or seat to receive a fluid collector insert so that the insert may be used intermittently or continuously in combination with the catheter.

Embodiments include a device for, and a method of, collecting fluids from a patient comprising placing, in a patient, a fluid collection device (e.g., catheter, tube, reservoir, appendage) that comprises a semipermeable membrane (e.g., hard, flexible, metal, ceramic, high strength, cellulose, polysulfone, dialysis membranes) that at least partially bounds (e.g., a sidewall of a container or tube, a part of a container, forms a container, forms a bag, forms a pocket) a lumen containing trapped osmotic solutes in aqueous solution (the trapped osmotic solutes can not pass out of the membrane, there is often an opening for removal, or a valve), with the lumen being in fluid communication with a transcutaneous port (through the skin) or percutaneous port (under the skin), wherein the trapped osmotic solutes have a molecular weight greater than a molecular weight cutoff of the semipermeable membrane and create an osmotic pressure that draws physiological fluid from the patient across the membrane and into the lumen. The osmotic solutes may be, for example, (a) present at a concentration to produce the osmotic pressure of between 50 and 100,000 Torr and/or (b) have an average molecular weight in a range from about 500 to about 50,000 (e.g., polymer with an average MW used as a trapped solute) and/or (c) trapped osmotic solutes are polymers and/or the concentration is from 1 millimolar to 10 molar. The port can be integral with the membrane (all one device connected together) or part of a system of components designed to cooperate with each other. For instance, the port can be connected up to an external reservoir that also contains the trapped osmotic solutes, with the physiological fluids passing also into the external reservoir. The osmotic pressure can make the fluids flow against gravity. The device can have membranes or inserts that are replaceable through a port, e.g., an insert as described. Internal channels in a reservoir can also be used to guide an insert or a fluid collection device through a reservoir. For instance, the port may be part of an internally implanted cage or internal reservoir and the fluid collection device is passed through the port and secured to (e.g., fastened, screwed into, put into a seat, snapped-in, force-fit) the cage or reservoir. The entire device or the part of the device that has the semipermeable membrane can be put in a tissue to withdraw fluid, e.g., peritoneal space, in an arm, in a leg, or in the patient at or near a lymph node or collection area that collects lung fluids.

Embodiments include a fluid collection system with a catheter or a needle and an insert that fits into the catheter or needle to create osmotic pressure that draws physiological fluid into the catheter or needed and can be secured therein, the system comprising a catheter or needle, an insert that comprises a collar having a bore that opens into a lumen at least partially bounded by a semipermeable membrane trapped osmotic solutes in the lumen to create osmotic pressure to draw fluids across the membrane into the lumen, wherein the membrane is joined to the collar, and the insert passes at least partially into the catheter or needle and the insert has a fastener and/or seat that mates with the catheter or needle to secure the insert. The needle or catheter can have openings, perforations, slots, or be just a cage, e.g., structural members that define a lumen.

As is evident, embodiments include (i) An assembly for a medical device that provides for fluid collection from a patient by osmotic pressure from trapped osmotic solutes contained within a semipermeable membrane that allows passage of native fluids from the patient across the membrane and into a lumen for removal of the fluid from the device, the assembly comprising a first opening and a second opening into an interior of a housing, an insert, wherein the insert is sized to pass through the first opening and into the interior, with the insert comprising a lumen at least partially bounded by a semipermeable membrane, and a fastener in a position to secure at least a portion of the insert within the housing with the lumen in fluid connection with the housing interior, wherein trapped osmotic solutes with a molecular weight greater than a molecular weight cut-off of the semipermeable membrane are trapped within the device when the first opening is in a closed disposition. (ii) The assembly of (i) wherein the fastener comprises a first set of threads on the insert that mates with a second set of threads on the housing. (iii) The assembly of (ii) wherein the first set of threads are external threads and the second set of threads are internal threads. (iv) The assembly of (iii) wherein the first opening is in a port on the housing that comprises a bore that comprises the internal threads, with the bore leading to the interior. (v) The assembly of (i) wherein the housing is a tube, hollow disk, or hollow ovoid. (vi) The assembly of (v) wherein the housing is the tube and the fastener comprises a seat in the tube and the insert comprises a flange to mate with the seat. (vii) The assembly of (v) wherein the housing is the tube and the membrane, when the insert is fastened to the tube, extends out of the tube. (viii) The assembly of (v) wherein the housing is the tube and the tube has threads on a proximal end and the insert is threadedly connectable to the external threads. (ix) The assembly of claim 1 wherein the insert comprises a collar that defines a bore, with the semipermeable membrane being connected to the collar and the lumen opening into the bore, with the collar comprising the fastener. (x) The assembly of (ix) wherein the collar has threads fastenable to threads on a port on the housing that comprises the first opening. (xi) The assembly of (ix) wherein the collar has threads fastenable to threads on a port on the housing that comprises the second opening. (xii) The assembly of (i) wherein the housing further comprises a guide that connects the first opening to the second opening, with the insert being passable through the first opening and the guide, with the fastener fastening the insert to the housing with at least a portion of the semipermeable membrane extending through the second opening and the lumen in fluid communication with the interior. (xiii) The assembly of (i) further comprising a tube affixed to a port that comprises the first opening or the second opening.

Other embodiments are (xiv) An implantable medical device that provides for fluid collection from a patient by osmotic pressure from trapped osmotic solutes contained within a semipermeable membrane that allows passage of native fluids from the patient across the membrane for removal of the fluid from the device, the device comprising an implantable reservoir comprising trapped osmotic solutes in fluid communication with a lumen at least partially bounded by a semipermeable membrane for flow of fluid from the patient across the membrane into the device, with the device having only one egress for the trapped osmotic solutes, with a port connected to the reservoir comprising said egress. (xv) The device of (xiv) wherein the port is a percutaneous or transcutaneous access port. (xvi) The device of (xiv) further comprising a filter in the port or a collar on the port. (xvii) The device of (xiv) wherein the reservoir interior is the lumen and the reservoir comprises the semipermeable membrane. (xviii) The device of (xiv) wherein a catheter attached to the reservoir comprises the lumen and the semipermeable membrane.

Other embodiments are (xix) A medical device that provides for fluid collection from a patient by osmotic pressure from trapped osmotic solutes contained within a semipermeable membrane that allows passage of native fluids from the patient across the membrane for removal of the fluid from the device, the device comprising an impermeable container containing trapped osmotic solutes in an aqueous solvent and an implant that also comprises the trapped osmotic solutes, the implant comprising a lumen at least partially bounded by a semipermeable membrane for flow of fluid from the patient across the membrane into the device, with the trapped osmotic solutes having a molecular weight greater than a molecular weight cut off of the semipermeable membrane. (xx) The device of (xix) further comprising a transcutaneous access port in the fluid connection between the implant and the reservoir. (xxi) The device of (xix) wherein the access port is the only egress for the trapped osmotic solutes. (xxii) The device of (xix) further comprising a filter in the port or a collar on the port. (xxiii) The device of (xix) wherein the reservoir interior is the lumen and the reservoir comprises the semipermeable membrane. (xxiv) The device of (xix) wherein the implant comprises a catheter that comprises the lumen and the semipermeable membrane. (xxv) The device of (xix) wherein the trapped osmotic solutes have a concentration to produce an osmotic pressure of at least 1.5 psi. (xxvi) A medical system for collection of a fluids comprising a tube with one opening with a wall of the tube comprising a semipermeable membrane.

Other embodiments are, e.g., (xxvii) A physiological fluid collection medical system comprising an external reservoir and an internally implantable container that has a lumen at least partially bounded by a semipermeable membrane having a molecular weight cut-off, with the lumen being in fluidly communication with the reservoir to contain trapped osmotic solutes that have a molecular weight greater than the molecular weight cut-off; or (xxviii) A physiological fluid collection medical system comprising an internally implantable container that is in fluid communication with a lumen at least partially bounded by a semipermeable membrane having a molecular weight cut-off to contain trapped osmotic solutes that have a molecular weight greater than the molecular weight cut-off, with the container comprising a percutaneous access port; or (xxix) A physiological fluid collection medical system comprising an insert and an internally implantable container that comprises a port having an opening that leads to an interior of the container, with the insert comprising a lumen at least partially bounded by a semipermeable membrane having a molecular weight cut-off to contain trapped osmotic solutes that have a molecular weight greater than the molecular weight cut-off, wherein the insert is passable through the port and disposable in the container in fluid communication with the container; or (xxx) A fluid collection system comprising a catheter or a needle and an insert that comprises a collar having a bore that opens into a lumen at least partially bounded by a semipermeable membrane to contain trapped osmotic solutes to remove fluids from the patient, with the membrane being joined to the collar, wherein the insert passes at least partially into the catheter or needle and the collar is securable to the catheter or needle; or (xxxi) A method of withdrawing fluid from a patient comprising implanting a device comprising trapped osmotic solutes in a lumen at least partially bounded by a semipermeable membrane to remove fluids from the patient; or (xxxii) A method of treating a wound comprising implanting a fluid collection device that comprises a semipermeable membrane and trapped osmotic solutes in the patient at or near the wound (for instance, in a tissue under an ulcer); or (xxxiii) A method of collecting fluids from a patient comprising placement of a fluid collection device that comprises a semipermeable membrane that at least partially bounds a lumen containing trapped osmotic solutes in the patient, with the lumen being in fluid communication with a transcutaneous port or percutaneous port, wherein the semipermeable membrane has a molecular weight cut-off that is no more than the molecular weight of the trapped osmotic solutes.

Other embodiments are one or more of (i) to (xxxiii) in combination with one or more features as follows: (xxxiv) wherein the trapped osmotic solutes are in aqueous solution; (xxxv) wherein the trapped osmotic solute concentration is more than about 4 millimolar; (xxxvi) wherein the trapped osmotic solute is in aqueous solution and has a molecular weight between about 500 and about 40,000; (xxxvii) The collection system of claim 31 wherein the molecular weight cut off is between about 1000 and about 50,000; wherein the container is a tube with one egress for the trapped osmotic solutes, with the egress being in fluid communication with the reservoir; (xxxviii) wherein the external reservoir is a rigid container with a volume of at least 50 ml or at least 200 ml or 100 ml to 5000 ml; (xxxix) wherein the implantable container (or tube or catheter or reservoir) has a volume of between about 55 and about 500 ml (xl) wherein connection of the external reservoir and the implantable container comprises a transcutaneous port that is reversibly connectable to the external reservoir; (xli) wherein the implantable container is an internal catheter that has one egress for the trapped solutes, with the egress being connected to an internally implanted reservoir that is in fluid communication with the lumen and the external reservoir (xlii) wherein the internally implanted reservoir comprises a semipermeable membrane for passage of fluids across the membrane into the reservoir; (xliii) comprising a tube connected to the (optionally internally implanted) reservoir for redirection of fluids out of the internal reservoir; (xliv) wherein the access port (or other port) comprises a self-sealing septum for sealing after puncture by a needle and/or a guard for preventing passage of a needle through the port; (xlv) wherein the lumen is the interior of the container and a wall of the container comprises the semipermeable membrane; (xlvi) wherein the trapped osmotic solutes are in aqueous solution in the lumen; (xlvii) wherein the molecular weight cut off is between about 1000 and about 50,000; (xlviii) wherein the container has a volume of about 55 to about 2000 ml and is made of an elastic biocompatible material impermeable to fluids; (xlix) wherein the implantable container comprises a seat to receive the insert; (l) wherein the seat is located on the port; (li) wherein the catheter comprises two portions that fit together; (lii) wherein the collar comprises threads that cooperate with threads on the catheter or needle; (liii) wherein the catheter or needle wall has a plurality of holes; (xliv) wherein the collar passes fully into the catheter or needle and seats therein; (lv) wherein the collar has threads that engage the catheter or needle without passing into an interior of the catheter or needle; (lvi) The system of claim 50 comprising the needle, with the needle sidewall comprising a plurality of openings (lvii) wherein the device comprises an external reservoir and the membrane is implanted, with the lumen being in fluid communication with the external reservoir, with osmotic pressure in the lumen and reservoir drawing physiological fluid from the patient across the membrane into the lumen and reservoir; (lviii) wherein the external reservoir is placed higher than the implanted membrane such that fluid collected from the patient flows against gravity into the reservoir (lix) wherein the fluid is withdrawn to treat edema; (lx) wherein the edema is upper limb edema resultant from breast cancer surgery; (lxi) wherein the edema results from ascites or congestive heart failure; (lxii) wherein the device is at least partially implanted in a peritoneal space and the fluid is withdrawn from the peritoneal space; (lxiii) wherein the osmotic solutes are present at a concentration to produce a predetermined osmotic pressure of between 1 and 100,000 Torr; (lxiv) wherein the trapped osmotic solutes have an average molecular weight in a range from about 500 to about 100,000; (lxv) wherein the trapped osmotic solutes are polymers; (lxvi) wherein the trapped osmotic solutes are not beads, and/or are not particles; (lxvii) placing a portion of the device that comprises the lumen into a tissue of the patient, wherein the tissue is a peritoneal space, in an arm, in a leg, or at or near a lymph node that collects lung fluids; (lxviii) wherein the port is placed in the patient and the portion of the medical device comprises the lumen is thereafter passed through the port into the patient; (lxix) wherein the port is part of a cage or reservoir and an insert that comprises the lumen in passed through the port and secured to the cage or reservoir; and (lxx) wherein the medical device that comprises the lumen is a catheter.

Embodiments include kits. The kits are collections of components designed to cooperate with each other. The kit may be housed in a single package (e.g., box, pouch, shipment box) or delivered as a collection of packages. The kit may have instructions for use of the component or components. Accordingly, an embodiment described herein may be provided as a kit and instructions for the same may also be included.

All patents, patent applications, and publications herein are hereby incorporated by reference herein to the extent they do not contradict what is explicitly disclosed herein. The invention has been described in terms of certain embodiments having a variety of features. The features may be mixed-and-matched to make further embodiments as guided by the need to make a functional device.

The invention claimed is:

1. A method of collecting fluids from a patient comprising
placing, in a patient, a fluid collection device that comprises a semipermeable membrane that at least partially bounds a lumen containing trapped osmotic solutes in aqueous solution,
with the lumen being in fluid communication with a transcutaneous port or percutaneous port,
wherein said port is part of an internally implanted cage or internal reservoir that is placed in the patient and the fluid collection device is thereafter passed through said port and secured to said cage or reservoir with a fastener that is chosen from the group consisting of threads, LUER-LOK, friction fit, mortise-and-tenon, tongue-and-groove, compression fit, and O-ring seal,
wherein the trapped osmotic solutes
have a molecular weight greater than a molecular weight cutoff of the semipermeable membrane,
create an osmotic pressure that draws physiological fluid from the patient across the membrane and into the lumen, and
are present at a concentration to produce the osmotic pressure at an amount between 50 and 100,000 Torr and are polymers with an average molecular weight between about 500 and about 5000.

2. The method of claim 1 comprising placing the semipermeable membrane of the fluid collection device in a peritoneal space, in an arm, in a leg, or in the patient at or near a lymph node that collects lung fluids.

3. The method of claim 1 wherein the fluid is withdrawn to treat edema or the fluid collection device is at least partially implanted in a peritoneal space and the fluid is withdrawn from the peritoneal space.

4. The method of claim 1 wherein the fastener comprises a thread.

5. A fluid collection system with a catheter or a needle and an insert that fits into the catheter or needle to create osmotic pressure that draws physiological fluid into the catheter or needed and can be secured therein, the system comprising:
a catheter or needle,
an insert that comprises a collar having a bore that opens into a lumen at least partially bounded by a semipermeable membrane, and
trapped osmotic solutes in the lumen to create osmotic pressure to draw fluids across the membrane into the lumen,
wherein the membrane is joined to the collar, and the insert passes at least partially into the catheter or needle and the insert has a fastener and/or seat that mates via threads with the catheter or needle to secure the insert.

6. The system of claim 5 wherein the semipermeable membrane passes out of a distal end of the catheter or needle when the collar is fastened to the catheter or needle.

7. The system of claim 5 wherein the trapped osmotic solutes are present at a concentration to produce the osmotic pressure of between 50 and 100,000 Torr.

8. The system of claim 5 wherein the trapped osmotic solutes have an average molecular weight in a range from about 500 to about 50,000.

9. The system of claim 5 wherein the trapped osmotic solutes comprise polymers.

10. The system of claim 5 wherein the trapped osmotic solute concentration is more than about 4 millimolar and has an average molecular weight between about 500 and about 100,000.

* * * * *